(12) United States Patent
Yokoyama et al.

(10) Patent No.: US 8,642,291 B2
(45) Date of Patent: Feb. 4, 2014

(54) METHOD FOR PRODUCING PROTEINS COMPRISING NON-NATURAL AMINO ACIDS INCORPORATED THEREIN

(75) Inventors: Shigeyuki Yokoyama, Kanagawa (JP); Kensaku Sakamoto, Yokohama (JP); Fumie Iraha, Yokohama (JP)

(73) Assignee: RIKEN, Wako-shi (JP)

( * ) Notice: Subject to any disclaimer, the term of this patent is extended or adjusted under 35 U.S.C. 154(b) by 0 days.

(21) Appl. No.: 13/470,752

(22) Filed: May 14, 2012

(65) Prior Publication Data
US 2012/0276589 A1 Nov. 1, 2012

Related U.S. Application Data

(63) Continuation of application No. 12/094,859, filed as application No. PCT/JP2006/324043 on Nov. 24, 2006, now Pat. No. 8,183,013.

(30) Foreign Application Priority Data

Nov. 24, 2005 (JP) ................................. 2005-338402

(51) Int. Cl.
| | | |
|---|---|---|
| *C12N 9/00* | (2006.01) | |
| *A61K 45/06* | (2006.01) | |
| *C12P 21/02* | (2006.01) | |
| *A61K 38/00* | (2006.01) | |

(52) U.S. Cl.
USPC ....... 435/69.1; 435/183; 435/254.2; 435/193; 435/320.1

(58) Field of Classification Search
None
See application file for complete search history.

(56) References Cited

FOREIGN PATENT DOCUMENTS

WO 2004 039989 5/2004
WO WO 2004/070024 A1 8/2004

OTHER PUBLICATIONS

Iraha, F. et al., "Exchanging of Tyroxyl-tRNA Synthetase Genes on the *E. coli* Chromosome for Facilitating the "Extended Genetic Code" Technology", Biology Society of Japan, p. 764 and 3P-1200 (2005).
Kobayashi, T. et al., "Structural Basis of Nonnatural Amino Acid Recognition by an Engineered Aminoacyl-tRNA Synthetase for Genetic Code Expansion", Proc. Natl. Acad. Sci., vol. 102, No. 5, pp. 1366-1371 and 10405 (2005).
Kiga, D. et al., "An Engineered *Escherichia coli* Tyrosyl-tRNA Synthetase for Site-Specific Incorporation of an Unnatural Amino Acid Into Proteins in Eukaryotic Translation and Its Application in a Wheat Germ Cell-Free System", Proc. Natl. Acad. Sci., vol. 99, No. 15, pp. 9715-9720 (2002).
Wang. L. et al., "Expanding the Genetic Code of *Escherichia coli*", Science, vol. 292, pp. 498-500 (2001).
Sakamoto, K. et al., "Site-Specific Incorporation of an Unnatural Amino Acid Into Proteins in Mammalian Cells", Nucleic Acids Reseach, vol. 30, No. 21, pp. 4692-4699 (2002).
Chin. J. et al., "An Expanded Eukaryotic Genetic Code", Science, vol. 301, pp. 964-967 (2003).
Santoro, S. et al., "An Efficient System for the Evolution of Aminoacyl-tRNA Synthetase Specificity", Nature Biotechnology, vol. 20, pp. 1044-1048 (2002).
Xie, J. et al., "The Site-Specific Incorporation of p-iodo-L-Phenylalanine Into Proteins for Structure Determination", Nature Biotechnology, vol. 22, No. 10, pp. 1297-1301 (2004).
Kobayashi, T. et al., "Structural Basis for Orthogonal tRNA Specificities of Tyrosyl-tRNA Synthetases for Genetic Code Expansion", Nature Structural Biology, vol. 10. No. 6, pp. 425-432 (2003).
Hino, N. et al., "Protein Photo-Cross-Linking in Mammalian Cells by Site-Specific Incorporation of a Photoreactive Amino Acid", Nature Methods, vol. 2, No. 3, pp. 201-206 (2005).
Sakamoto, K et al., "Tokushu Proteorne Soyaku to DDS Jinko Inden Ango System o Riyo Shita Kinosei Tanpakushitsu No Sakusei", vol. 18, No. 6, pp. 502-510 (2003).
Xie, J. et al., "A Chemical Toolkit for Proteins—An Expanded Genetic Code", Nature Reviews Molecular Cell Biology, vol. 7, pp. 775-782 (2006).
Jianming Xie, et al., "An expanding genetic code", Methods, Elsevier, vol. 36, No. 3, XP-004997375, Jul. 1, 2005, pp. 227-238.
Thomas J. Magliery, "Unnatural Protein Engineering: Producing Proteins with Unnatural Amino Acids" Medicinal Chemistry Reviews—Online, vol. 2, No. 4, XP003005033, Jan. 1, 2005, pp. 303-323.
Ulrich Hahn, et al., "Old Codons, New Amino Acids Angewandte Chemie—International Edition", vol. 43, No. 10, XP-002529850, Feb. 27, 2004, pp. 1190-1193.
Anne Strømgaard, et al., "Site-Specific Incorporation of Unnatural Amino Acids into Proteins" ChemBioChem, A European Journal of Chemical Biology, vol. 5, No. 7, XP-002529851, Jul. 5, 2004, pp. 909-916.

(Continued)

*Primary Examiner* — Kagnew H Gebreyesus
(74) *Attorney, Agent, or Firm* — Oblon, Spivik, McClelland, Maier & Neustadt, L.L.P.

(57) ABSTRACT

Producing proteins incorporating non-natural amino acids can involve introducing genes into and knocking inherent genes out of eukaryote-type cells. Genes to be introduced include genes encoding eukaryote-type aminoacyl tRNA synthetase mutants having enhanced specificity to non-natural amino acids, compared with specificity to similar natural amino acids, and tRNA genes for non-natural amino acids capable of binding to the non-natural amino acids in the presence of the eukaryote-type aminoacyl tRNA synthetase mutants. Inherent genes to be knocked out include genes encoding aminoacyl tRNA synthetase having specificity to natural amino acids and tRNA genes capable of binding to the natural amino acids in the presence of the inherent aminoacyl tRNA synthetase.

11 Claims, 3 Drawing Sheets

(56) References Cited

OTHER PUBLICATIONS

Anne K. Kowal, et al., "Exploiting unassigned codons in *Micrococcus luteus* for tRNA-based amino acid mutagenesis", Oxford University Press, Nucleic Acids Research, vol. 25, No. 22, XP-001145471, Nov. 15, 1997, pp. 4685-4689.

Deqiang Zhang, et al., "Structure-based design of mutant *Methanococcus jannaschii* tyrosyl-tRNA synthetase for incorporation of O-methyl-$_L$-tyrosine" Proceedings of the National Academy of Sciences, vol. 99, No. 10, XP-002976470, May 14, 2002, pp. 6579-6584.

Chang C. Liu et al., "Adding New Chemistries to the Genetic Code", Reviews in Advance, Mar. 9, 2010, Annu. Rev. Biochem., 2010, pp. 79:15.1-15.32.

Fumie Iraha, et al., "Functional Replacement of the Endogenous tyrosyl-tRNA synthetase-tRNA Tyr pair by the Archaeal Tyrosine pair in *Escherichia coli* for Genetic Code Expansion", Nucleic Acids Research, 2010, vol. 38, No. 11, pp. 3682-3691.

Jason W. Chin, et al., "An Expanded Eukaryotic Genetic Code", Science, Aug. 15, 2003, vol. 301, pp. 964-967.

Jason W. Chin, et al., "An Expanded Eukaryotic Genetic Code", Supplementary Online Material, Science 301, 964, 2003.

SEQUENCE LISTING

```
<160> NUMBER OF SEQ ID NOS: 27

<210> SEQ ID NO 1
<211> LENGTH: 5885
<212> TYPE: DNA
<213> ORGANISM: Methanococcus jannaschii
<220> FEATURE:
<221> NAME/KEY: CDS
<222> LOCATION: (3284)..(4204)
<220> FEATURE:
<221> NAME/KEY: tRNA
<222> LOCATION: (4334)..(4410)
<220> FEATURE:
<221> NAME/KEY: CDS
<222> LOCATION: (4847)..(5662)

<400> SEQUENCE: 1
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
```

```
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaaccdtt   1320 cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
atatcgtcca ttccgacagc atcgccagtc actatgcgt gctgctagcg ctatatgcgt    1740
tgatgcaatt tctatgcgca cccgttctcg gagcactgtc cgaccgcttt ggccgccgcc    1800
cagtcctgct cgcttcgcta cttggagcca ctatcgacta cgcgatcatg gcgaccacac    1860
ccgtcctgtg gatcctctac gccggacgca tcgtggccgg catcaccggc gccacaggtg    1920
cggttgctgg cgcctatatc gccgacatca ccgatgggga agatcgggct cgccacttcg    1980
ggctcatgag cgcttgtttc ggcgtgggta tggtggcagg ccccgtggcc gggggactgt    2040
tgggcgccat ctccttgcat gcaccattcc ttgcggcggc ggtgctcaac ggcctcaacc    2100
tactactggg ctgcttccta atgcaggagt cgcataaggg agagcgtcga agctttaatg    2160
cggtagttta tcacagttaa attgctaacg cagtcaggca ccgtgtatga aatctaacaa    2220
tgcgctcatc gtcatcctcg gcaccgtcac cctggatgct gtaggcatag gcttggttat    2280
gccggtactg ccgggcctct tgcgggatat cgtccattcc gacagcatcg ccagtcacta    2340
tggcgtgctg ctagcatcga cgagtctggc tttgacattc gactagaagt ggacggtggc    2400
gtgaaggtga acaacattgg cgaaatcgct gcggcgggcg cggatatgtt cgtcgccggt    2460
tcggcaatct tgaccagcca gactacaaaa aagtcattga tgaaatgcgc agtgaactgg    2520
caaaggtaag tcatgaataa gtttgaagat attcgcggcg tcgcttttga tcttgatggt    2580
acgctggtcg acagtgctcc tggtcttgct gctgcggtag atatggcgct gtatgcgctg    2640
gagttgcccg tcgcaggtga agaacgcgtt attacctgga ttggtaacgg cgcagatgtt    2700
ctgatggagc gcgcattgac ctgggcgcgt caggaacgtg cgactcagcg taaaacaatg    2760
ggtaaaccgc ccgttgatga cgacattccg gcagaagaac aggtacgtat tctgcgtaaa    2820
ctgttcgatc gctactatgg cgaggttgcc gaagagggga cgttttttgtt cccgcacgtt    2880 gccgatacgt tgggcgcgtt gcaggctaaa ggcctgccgc taggcctggt caccaacaaa    2940
ccgacgccgt tcgtcgcgcc gctgctcgaa gccttagata tcgccaaata cttcagcgtg    3000
gtgattggtg gtgatgatgt gcaaaacaaa aaaccgcatc cggacccgct gttactggtg    3060
gctgagcgga tgggaattgc cccacaacag atgctgtttg tcggcgactc acgcaatgat    3120
attcaggcgg caaaagcggc aggttgccca tcagttggct taacctacgg atataactac    3180
ggcgaggcta tcgatctcag ccagcctgat gtaatttatc agtctataaa tgaccttctg    3240
cccgcattag ggcttccgca tagcgaaaat caggaatcga cat atg gac gaa ttt    3295
                                              Met Asp Glu Phe
                                                1 gaa atg ata aag aga aac aca tct gaa att atc agc gag gaa gag tta    3343
```

-continued

```
        Glu Met Ile Lys Arg Asn Thr Ser Glu Ile Ile Ser Glu Glu Glu Leu
        5                   10                  15                  20 aga gag gtt tta aaa aaa gat gaa aaa tct gct tac ata ggt ttt gaa              3391
Arg Glu Val Leu Lys Lys Asp Glu Lys Ser Ala Tyr Ile Gly Phe Glu
                25                  30                  35 cca agt ggt aaa ata cat tta ggg cat tat ctc caa ata aaa aag atg              3439
Pro Ser Gly Lys Ile His Leu Gly His Tyr Leu Gln Ile Lys Lys Met
        40                  45                  50 att gat tta caa aat gct gga ttt gat ata att ata ttg ttg gct gat              3487
Ile Asp Leu Gln Asn Ala Gly Phe Asp Ile Ile Ile Leu Leu Ala Asp
            55                  60                  65 tta cac gcc tat tta aac cag aaa gga gag ttg gat gag att aga aaa              3535
Leu His Ala Tyr Leu Asn Gln Lys Gly Glu Leu Asp Glu Ile Arg Lys
    70                  75                  80 ata gga gat tat aac aaa aaa gtt ttt gaa gca atg ggg tta aag gca              3583
Ile Gly Asp Tyr Asn Lys Lys Val Phe Glu Ala Met Gly Leu Lys Ala
85                  90                  95                  100 aaa tat gtt tat gga agt gaa ttc cag ctt gat aag gat tat aca ctg              3631
Lys Tyr Val Tyr Gly Ser Glu Phe Gln Leu Asp Lys Asp Tyr Thr Leu
                105                 110                 115 aat gtc tat aga ttg gct tta aaa act acc tta aaa aga gca aga agg              3679
Asn Val Tyr Arg Leu Ala Leu Lys Thr Thr Leu Lys Arg Ala Arg Arg
        120                 125                 130 agt atg gaa ctt ata gca aga gag gat gaa aat cca aag gtt gct gaa              3727
Ser Met Glu Leu Ile Ala Arg Glu Asp Glu Asn Pro Lys Val Ala Glu
            135                 140                 145 gtt atc tat cca ata atg cag gtt aat gat att cat tat tta ggc gtt              3775
Val Ile Tyr Pro Ile Met Gln Val Asn Asp Ile His Tyr Leu Gly Val
    150                 155                 160 gat gtt gca gtt gga ggg atg gag cag aga aaa ata cac atg tta gca              3823
Asp Val Ala Val Gly Gly Met Glu Gln Arg Lys Ile His Met Leu Ala
165                 170                 175                 180 agg gag ctt tta cca aaa aag gtt gtt tgt att cac aac cct gtc tta              3871
Arg Glu Leu Leu Pro Lys Lys Val Val Cys Ile His Asn Pro Val Leu
                185                 190                 195 acg ggt ttg gat gga gaa gga aag atg agt tct tca aaa ggg aat ttt              3919
Thr Gly Leu Asp Gly Glu Gly Lys Met Ser Ser Ser Lys Gly Asn Phe
        200                 205                 210 ata gct gtt gat gac tct cca gaa gag att agg gct aag ata aag aaa              3967
Ile Ala Val Asp Asp Ser Pro Glu Glu Ile Arg Ala Lys Ile Lys Lys
            215                 220                 225 gca tac tgc cca gct gga gtt gtt gaa gga aat cca ata atg gag ata              4015
Ala Tyr Cys Pro Ala Gly Val Val Glu Gly Asn Pro Ile Met Glu Ile
    230                 235                 240 gct aaa tac ttc ctt gaa tat cct tta acc ata aaa agg cca gaa aaa              4063
Ala Lys Tyr Phe Leu Glu Tyr Pro Leu Thr Ile Lys Arg Pro Glu Lys
245                 250                 255                 260 ttt ggt gga gat ttg aca gtt aat agc tat gag gag tta gag agt tta              4111
Phe Gly Gly Asp Leu Thr Val Asn Ser Tyr Glu Glu Leu Glu Ser Leu
                265                 270                 275 ttt aaa aat aag gaa ttg cat cca atg gat tta aaa aat gct gta gct              4159
Phe Lys Asn Lys Glu Leu His Pro Met Asp Leu Lys Asn Ala Val Ala
        280                 285                 290 gaa gaa ctt ata aag att tta gag cca att aga aag aga tta taa                  4204
Glu Glu Leu Ile Lys Ile Leu Glu Pro Ile Arg Lys Arg Leu
            295                 300                 305 gatctgccag acattaacgc ttctggagaa actcaacgag ctggacgcgg atgaacaggc            4264
agacatctgt gaatcgcttc acgaccacgc atcaaaaaaa atccttagct ttcgctaagg            4324
attttatttt ggtccggcgg gccggatttg aaccagcgac atgcgatct acagtccgcc             4384
```

```
gttctaccag gctgaactac cgccggagga aagttacaag tattacacaa agttttttat    4444
gttgagaata ttttttgat gggaaggcac ttatttttga tcgttcgctc aaagaagcct    4504
cgagtcactt tcggccgagg tctgcctcgt gaagaaggtg ttgctgactc ataccaggcc    4564
tgaatcgccc catcatccag ccagaaagtg agggagccac ggttgatgag agctttgttg    4624
taggtggacc agttggtgat tttgaacttt tgctttgcca cggaacggtc tgcgttgtcg    4684
ggaagatgcg tgatctgatc cttcaactca gcaaaagttc gatttattca acaaagccac    4744
gttgtgtctc aaaatctctg atgttacatt gcacaagata aaatatatc atcatgaaca    4804 ataaaactgt ctgcttacat aaacagtaat acaagggtg tt atg agc cat att       4858
                                             Met Ser His Ile
                                                          310 caa cgg gaa acg tct tgc tcg aag ccg cga tta aat tcc aac atg gat    4906
Gln Arg Glu Thr Ser Cys Ser Lys Pro Arg Leu Asn Ser Asn Met Asp
            315                 320                 325 gct gat tta tat ggg tat aaa tgg gct cgc gat aat gtc ggg caa tca    4954
Ala Asp Leu Tyr Gly Tyr Lys Trp Ala Arg Asp Asn Val Gly Gln Ser
        330                 335                 340 ggt gcg aca atc tat cga ttg tat ggg aag ccc gat gcg cca gag ttg    5002
Gly Ala Thr Ile Tyr Arg Leu Tyr Gly Lys Pro Asp Ala Pro Glu Leu
    345                 350                 355 ttt ctg aaa cat ggc aaa ggt agc gtt gcc aat gat gtt aca gat gag    5050
Phe Leu Lys His Gly Lys Gly Ser Val Ala Asn Asp Val Thr Asp Glu
360                 365                 370 atg gtc aga cta aac tgg ctg acg gaa ttt atg cct ctt ccg acc atc    5098
Met Val Arg Leu Asn Trp Leu Thr Glu Phe Met Pro Leu Pro Thr Ile
375                 380                 385                 390 aag cat ttt atc cgt act cct gat gat gca tgg tta ctc acc act gcg    5146
Lys His Phe Ile Arg Thr Pro Asp Asp Ala Trp Leu Leu Thr Thr Ala
            395                 400                 405 atc ccc ggg aaa aca gca ttc cag gta tta gaa gaa tat cct gat tca    5194
Ile Pro Gly Lys Thr Ala Phe Gln Val Leu Glu Glu Tyr Pro Asp Ser
        410                 415                 420 ggt gaa aat att gtt gat gcg ctg gca gtg ttc ctg cgc cgg ttg cat    5242
Gly Glu Asn Ile Val Asp Ala Leu Ala Val Phe Leu Arg Arg Leu His
    425                 430                 435 tcg att cct gtt tgt aat tgt cct ttt aac agc gat cgc gta ttt cgt    5290
Ser Ile Pro Val Cys Asn Cys Pro Phe Asn Ser Asp Arg Val Phe Arg
440                 445                 450 ctc gct cag gcg caa tca cga atg aat aac ggt ttg gtt gat gcg agt    5338
Leu Ala Gln Ala Gln Ser Arg Met Asn Asn Gly Leu Val Asp Ala Ser
455                 460                 465                 470 gat ttt gat gac gag cgt aat ggc tgg cct gtt gaa caa gtc tgg aaa    5386
Asp Phe Asp Asp Glu Arg Asn Gly Trp Pro Val Glu Gln Val Trp Lys
            475                 480                 485 gaa atg cat aag ctt ttg cca ttc tca ccg gat tca gtc gtc act cat    5434
Glu Met His Lys Leu Leu Pro Phe Ser Pro Asp Ser Val Val Thr His
        490                 495                 500 ggt gat ttc tca ctt gat aac ctt att ttt gac gag ggg aaa tta ata    5482
Gly Asp Phe Ser Leu Asp Asn Leu Ile Phe Asp Glu Gly Lys Leu Ile
    505                 510                 515 ggt tgt att gat gtt gga cga gtc gga atc gca gac cga tac cag gat    5530
Gly Cys Ile Asp Val Gly Arg Val Gly Ile Ala Asp Arg Tyr Gln Asp
520                 525                 530 ctt gcc atc cta tgg aac tgc ctc ggt gag ttt tct cct tca tta cag    5578
Leu Ala Ile Leu Trp Asn Cys Leu Gly Glu Phe Ser Pro Ser Leu Gln
535                 540                 545                 550 aaa cgg ctt ttt caa aaa tat ggt att gat aat cct gat atg aat aaa    5626
```

```
Lys Arg Leu Phe Gln Lys Tyr Gly Ile Asp Asn Pro Asp Met Asn Lys
            555                 560                 565 ttg cag ttt cat ttg atg ctc gat gag ttt ttc taa tcagaattgg         5672
Leu Gln Phe His Leu Met Leu Asp Glu Phe Phe
            570                 575 ttaattggtt gtaacactgg cagagcatta cgctgacttg acgggacggc ggctttgttg  5732
aataaatcgc attcgccatt caggctgcgc aactgttggg aagggcgatc ggtgcgggcc  5792
tcttcgctat tacgccagct ggcgaaaggg ggatgtgctg caaggcgatt aagttgggta  5852
acgccagggt tttcccagtc acgacgttgt aaa                               5885

<210> SEQ ID NO 2
<211> LENGTH: 306
<212> TYPE: PRT
<213> ORGANISM: Methanococcus jannaschii

<400> SEQUENCE: 2

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Tyr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300
```

Arg Leu
305

<210> SEQ ID NO 3
<211> LENGTH: 271
<212> TYPE: PRT
<213> ORGANISM: Methanococcus jannaschii

<400> SEQUENCE: 3

Met Ser His Ile Gln Arg Glu Thr Ser Cys Ser Lys Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcgtggaa gattgatcgt cttgcaccct gaaaagatgc aaaaatcttg                 50

<210> SEQ ID NO 5
<211> LENGTH: 50
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 5
acagggaaca tgatgaaaaa tattctcgct atccagtctc acgttgttta              50

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atgcgtggaa gattgatcgt cttgcaccct gaaaagatgc aaaaatcttg acccgacgca   60
ctttgcgccg                                                          70

<210> SEQ ID NO 7
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taaacaacgt gagactggat agcgagaata ttttcatca tgttccctgt ttacgccccg    60
ccctgccact c                                                        71

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaataactg gttaccttta atccgttacg gatgaaaatt acgcaaccag              50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agtccctgaa cttcccaacg aatccgcaat taaatattct gcccatgcgg              50

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaataactg gttaccttta atccgttacg gatgaaaatt acgcaaccag acccgacgca   60
ctttgcgccg                                                          70
```

<210> SEQ ID NO 11
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgcatgggc agaatattta attgcggatt cgttgggaag ttcagggact ttacgccccg    60
ccctgccact c                                                        71

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtaatcagta ggtcaccagt tcgattccgg tagtcggcac catcaagtcc               50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggccacgcga tggcgtagcc cgagacgata agttcgctta ccggctcgaa               50

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtaatcagta ggtcaccagt tcgattccgg tagtcggcac catcaagtcc gattttcagg    60
agctaaggaa gc                                                       72

<210> SEQ ID NO 15
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttcgagccgg taagcgaact tatcgtctcg ggctacgcca tcgcgtggcc ttacgccccg    60
ccctgccact c                                                        71

<210> SEQ ID NO 16
<211> LENGTH: 886
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
acccgacgca ctttgcgccg aataaatacc tgtgacggaa gatcacttcg cagaataaat      60
aaatcctggt gtccctgttg ataccgggaa gccctgggcc aacttttggc gaaaatgaga     120
cgttgatcgg cacgtaagag gttccaactt tcaccataat gaaataagat cactaccggg     180
cgtatttttt gagttatcga gattttcagg agctaaggaa gctaaaatgg agaaaaaaat     240
cactggatat accaccgttg atatatccca atggcatcgt aaagaacatt ttgaggcatt     300
tcagtcagtt gctcaatgta cctataacca gaccgttcag ctggatatta cggcctttttt    360 aaagaccgta agaaaaaata agcacaagtt ttatccggcc tttattcaca ttcttgcccg     420
cctgatgaat gctcatccgg aattccgtat ggcaatgaaa gacggtgagc tggtgatatg     480
ggatagtgtt cacccttgtt acaccgtttt ccatgagcaa actgaaacgt tttcatcgct     540
ctggagtgaa taccacgacg atttccggca gtttctacac atatattcgc aagatgtggc     600
gtgttacggt gaaaacctgg cctatttccc taaagggttt attgagaata tgttttttcgt    660 ctcagccaat ccctgggtga gtttcaccag ttttgattta aacgtggcca atatggacaa     720
cttcttcgcc cccgttttca ccatgggcaa atattatacg caaggcgaca aggtgctgat     780
gccgctggcg attcaggttc atcatgccgt ctgtgatggc ttccatgtcg cagaatgct      840 taatgaatta caacagtact gcgatgagtg gcagggcggg gcgtaa                   886
```

<210> SEQ ID NO 17  
<211> LENGTH: 686  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 17

```
gattttcagg agctaaggaa gctaaaatgg agaaaaaaat cactggatat accaccgttg      60
atatatccca atggcatcgt aaagaacatt ttgaggcatt tcagtcagtt gctcaatgta    120
cctataacca gaccgttcag ctggatatta cggcctttttt aaagaccgta agaaaaaata   180
agcacaagtt ttatccggcc tttattcaca ttcttgcccg cctgatgaat gctcatccgg    240
aattccgtat ggcaatgaaa gacggtgagc tggtgatatg ggatagtgtt cacccttgtt   300
acaccgtttt ccatgagcaa actgaaacgt tttcatcgct ctggagtgaa taccacgacg    360
atttccggca gtttctacac atatattcgc aagatgtggc gtgttacggt gaaaacctgg    420
cctatttccc taaagggttt attgagaata tgttttttcgt ctcagccaat ccctgggtga   480
gtttcaccag ttttgattta aacgtggcca atatggacaa cttcttcgcc cccgttttca    540
ccatgggcaa atattatacg caaggcgaca aggtgctgat gccgctggcg attcaggttc    600
atcatgccgt ctgtgatggc ttccatgtcg cagaatgct taatgaatta caacagtact    660
gcgatgagtg gcagggcggg gcgtaa                                          686
```

<210> SEQ ID NO 18  
<211> LENGTH: 735  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 18

```
atggctagca tgactggtgg acagcaaatg ggtcgggatc cgggtgcgaa ttctggtgta      60
actaagaact cttagagccc tatactaggt tattggaaaa ttaagggcct tgtgcaaccc    120
```

```
actcgacttc ttttggaata tcttgaagaa aaatatgaag agcatttgta tgagcgcgat      180
gaaggtgata aatggcgaaa caaaaagttt gaattgggtt tggagtttcc caatcttcct      240
tattatattg atggtgatgt taaattaaca cagtctatgg ccatcatacg ttatatagct      300
gacaagcaca acatgttggg tggttgtcca aaagagcgtg cagagatttc aatgcttgaa      360
ggagcggttt tggatattag atacggtgtt tcgagaattg catatagtaa agactttgaa      420
actctcaaag ttgattttct tagcaagcta cctgaaatgc tgaaaatgtt cgaagatcgt      480
ttatgtcata aaacatattt aaatggtgat catgtaaccc atcctgactt catgttgtat      540
gacgctcttg atgttgtttt atacatggac ccaatgtgcc tggatgcgtt cccaaaatta      600
gtttgtttta aaaacgtat tgaagctatc ccacaaattg ataagtactt gaaatccagc       660
aagtatatag catggccttt gcagggctgg caagccacgt tggtggtgg cgaccatcct      720 ccaaaatcgg attaa                                                       735

<210> SEQ ID NO 19
<211> LENGTH: 4324
<212> TYPE: DNA
<213> ORGANISM: Esherichia coli

<400> SEQUENCE: 19
gaattccgga tgagcattca tcaggcgggc aagaatgtga ataaaggccg gataaaactt       60
gtgcttattt ttcttttacgg tctttaaaaa ggccgtaata tccagctgaa cggtctggtt      120
ataggtacat tgagcaactg actgaaatgc ctcaaaatgt tctttacgat gccattggga      180
tatatcaacc taggtatatc ccatgatttt tttctccatt ttagcttcct tagctcctga      240
aaatctcgat aactcaaaaa atcgcccggg tagtgatctt attcattat ggtgaaagtt       300 ggaacctctt acgtgccgat caacgtctca ttttcgccaa aagttggccc agggcttccc      360
ggtatcaaca gggacaccag gatttattta ttctgcgaag tgatcttccg tcacaggtat      420
ttattcggcg caaagtgcgt cgggtgatgc tgccaactta ctgatttagt gtatgatggt      480
gtttttgagg tgctccagtg gcttctgttt ctatcagctg tccctcctgt tcagctactg      540
acggggtggt gcgtaacggc aaaagcaccg ccggacatca gcgctagcgg agtgtatact      600
ggcttactat gttggcactg atgagggtgt cagtgaagtg cttcatgtgg caggagaaaa      660
aaggctgcac cggtgcgtca gcagaatatg tgatacagga tatattccgc ttcctcgctc      720
actgactcgc tacgctcggt cgttcgactg cggcgagcgg aaatggctta cgaacggggc      780
ggagatttcc tggaagatgc caggaagata cttaacaggg aagtgagagg gccgcggcaa      840
agccgttttt ccataggctc cgcccccctg acaagcatca cgaaatctga cgctcaaatc      900
agtggtggcg aaacccgaca ggactataaa gataccaggc gtttccccct ggcggctccc      960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactgcag cagccactgg taattgattt      1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta gcgcagacc      1380 aaaacgatct caagaagatc atcttattaa tcagataaaa tatttctaga tttcagtgca     1440
atttatctct tcaaatgtag cacctgaagt cagccccata cgatataagt tgtaattctc     1500
```

```
atgtttgaca gcttatcatc gataagcttg atgcgtggaa gattgatcgt cttgcaccct    1560
gaaaagatgc aaaaatcttg ctttaatcgc tggtactcct gattctggca ctttattcta    1620
tgtctctttc gcatctggcg aaaagtcgtt taccggcaaa ggtgcagtcg ttatatactt    1680
ggagattcat atgttccagc ttgatgcgtg aagattgat cgtcttgcac cctgaaaaga    1740
tgcaaaaatc ttgctttaat cgctggtact cctgattctg cactttat tctatgtctc    1800 tttcgcatct ggcgaaaagt cgtgtaccgg caaggtgcag tcgttatata cttgagattc    1860
atatgttcct tagatctgga tcctctacgc cggacgcatc gtggccggca tcaccggcgc    1920
cacaggtgcg gttgctggcg cctatatcgc cgacatcacc gatggggaag atcgggctcg    1980
ccacttcggg ctcatgaggc atgcggcgcc gcttctttga gcgaacgatc aaaaataagt    2040
ggcgccccat caaaaaaata ttctcaacat aaaaaacttt gtgtaatact tgtaacgctg    2100
ccatcagacg cattggtggg gttcccgagc ggccaaaggg agcagactct aaatctgccg    2160
tcatcgactt cgaaggttcg aatccttccc ccaccaccat ttatcagatt ggaaattttt    2220
gatccttagc gaaagctaag gatttttttt agtcgaccga tgcccttgag agccttcaac    2280
ccagtcagct ccttccggtg ggcgcggggc atgactatcg tcgccgcact tatgactgtc    2340
ttctttatca tgcaactcgt aggacaggtg ccggcagcgc tctgggtcat tttcggcgag    2400
gaccgctttc gctggagcgc gacgatgatc ggcctgtcgc ttgcggtatt cggaatcttg    2460
cacgccctcg ctcaagcctt cgtcactggt cccgccacca aacgtttcgg cgagaagcag    2520
gccattatcg ccggcatggc ggccgaggcc atccagcctc gcgtcgcgat aaaaaaaatc    2580
cttagctttc gctaaggatc aaaaattcc aaagtgttac aaccaattaa ccaattctga    2640
ttagaaaaac tcatcgagca tcaaatgaaa ctgcaattta ttcatatcag gattatcaat    2700
accatatttt tgaaaaagcc gtttctgtaa tgaaggagaa aactcaccga ggcagttcca    2760
taggatggca agatcctggt atcggtctgc gattccgact cgtccaacat caatacaacc    2820
tattaatttc ccctcgtcaa aaataaggtt atcaagtgag aaatcaccat gagtgacgac    2880
tgaatccggt gagaatggca aaagcttatg catttctttc cagacttgtt caacaggcca    2940
gccattacgc tcgtcatcaa aatcactcgc atcaaccaaa ccgttattca ttcgtgattg    3000
cgcctgagcg agacgaaata cgcgatcgct gttaaaagga caattacaaa caggaatcga    3060
atgcaaccgg cgcaggaaca ctgccagcgc atcaacaata ttttcacctg aatcaggata    3120
ttcttctaat acctggaatg ctgttttccc ggggatcgca gtggtgagta accatgcatc    3180
atcaggagta cggataaaat gcttgatggt cggaagaggc ataaattccg tcagccagtt    3240
tagtctgacc atctcatctg taacatcatt ggcaacgcta cctttgccat gtttcagaaa    3300
caactctggc gcatcgggct tcccatacaa tcgatagatt gtcgcacctg attgcccgac    3360
attatcgcga gcccatttat acccatataa atcagcatcc atgttggaat ttaatcgcgg    3420
cttcgagcaa gacgtttccc gttgaatatg gctcataaca ccccttgtat tactgtttat    3480
gtaagcagac agttttattg ttcatgatga tatattttta tcttgtgcaa tgtaacatca    3540
gagattttga gacacaacgt ggctttgttg aataaatcga acttttgctg agttgaagga    3600
tcagatcacg catcttcccg acaacgcaga ccgttccgtg gcaaagcaaa agttcaaaat    3660
caccaactgg tccacctaca acaaagctct catcaaccgt ggctcgctca ctttctggct    3720
ggatgatggg gcgattcagg cctggtatga gtcagcaaca ccttcttcac gagggacgac    3780
cgggtcgaat ttgctttcga atttctgcca ttcatccgct tattatcact tattcaggcg    3840
tagcaccagg cgtttaaggg caccaataac tgccttaaaa aaattacgcc ccgccctgcc    3900
```

```
actcatcgca gtactgttgt aattcattaa gcattctgcc gacatggaag ccatcacaga    3960
cggcatgatg aacctgaatc gccagcggca tcagcacctt gtcgccttgc gtataatatt    4020
tgcccatggt gaaaacgggg gcgaagaagt tgtccatatt ggccacgttt aaatcaaaac    4080
tggtgaaact cacccaggga ttggctgaga cgaaaaacat attctcaata aaccctttag    4140
ggaaataggc caggttttca ccgtaacacg ccacatcttg cgaatatatg tgtagaaact    4200
gccggaaatc gtcgtggtat tcactccaga gcgatgaaaa cgtttcagtt tgctcatgga    4260
aaacggtgta acaagggtga acactatccc atatcaccag ctcaccgtct ttcattgcca    4320
tacg                                                                4324
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcaggacgtt attcatgtcg                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gggacttttg aaagtgatgg                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gtaatcagta ggtcaccagt                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ttcgagccgg taagcgaact                                                  20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 24

```
<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
taaacaacgt gagactggat ag                                              22

<210> SEQ ID NO 26
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggtggggttc ccgagcggcc aaagggagca gactctaaat ctgccgtcat cgacttcgaa      60
ggttcgaatc cttcccccac cacca                                            85

<210> SEQ ID NO 27
<211> LENGTH: 261
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gcatgcggcg ccgcttcttt gagcgaacga tcaaaaataa gtggcgcccc atcaaaaaaa      60
tattctcaac ataaaaaact ttgtgtaata cttgtaacgc tgccatcaga cgcattggtg     120
gggttcccga gcggccaaag ggagcagact ctaaatctgc cgtcatcgac ttcgaaggtt     180
cgaatccttc ccccaccacc atttatcaca gattggaaat ttttgatcct tagcgaaagc     240
taaggatttt ttttagtcga c                                               261
```

METHOD FOR PRODUCING PROTEINS COMPRISING NON-NATURAL AMINO ACIDS INCORPORATED THEREIN

CROSS-REFERENCE TO RELATED APPLICATIONS

This application is a continuation of U.S. 12/094,859 filed Jan. 5, 2009, now U.S. Pat. No. 8,183,013, which is a National Stage of PCT/JP2006/324043 filed Nov. 24, 2006.

TECHNICAL FIELD

The present invention relates to a method for producing proteins into which non-natural amino acids have been incorporated at desired positions, host cells used for such method, and a reagent kit for cell-free protein synthesis used for such method.

BACKGROUND ART

The natural proteins are made up of naturally-occurring 20 amino acid species (hereafter referred to as "natural amino acids"). When protein structures or functions are analyzed or chemical behavior thereof is extended, amino acids that are not present in nature (hereafter referred to as "non-natural amino acids") may be incorporated into desired positions of an amino acid sequence. Proteins into which non-natural amino acids have been incorporated are referred to as "alloproteins."

Aminoacyl tRNA synthetase (hereafter referred to as "aaRS") is an enzyme that binds a given amino acid specifically to given tRNA. Except for certain exceptional instances, 20 different types of such enzymes exist corresponding to each of 20 natural amino acid species. When alloproteins are to be synthesized, new aaRS corresponding to non-natural amino acids (hereafter referred to as "aaRS*") and tRNA paired with a codon that does not encode natural amino acids (hereafter referred to as "tRNA*") need to be incorporated into host cells to make them properly function therein. That is, tRNA* to which non-natural amino acids have been bound with the aid of aaRS* can be paired with a codon that does not naturally encode natural amino acids in host cells, in order to synthesize alloproteins into which non-natural amino acids have been incorporated.

In such a case, aaRS* is prepared based on existing aaRS that is specific for a given natural amino acid by modifying functions thereof so as to have activity of recognizing a non-natural amino acid similar to the given natural amino acid as a substrate. When aaRS* that is specific for O-methyltyrosine (i.e., a non-natural amino acid) similar to tyrosine (i.e., a natural amino acid) is to be prepared, for example, TyrRS mutant having enhanced specificity to o-methyltyrosine is prepared based on existing tyrosyl-tRNA synthetase (TyrRS). When alloproteins are synthesized with the use of such aaRS*, use of aaRS* that does not react with 20 natural amino acid species inherent in the host cells and tRNAs corresponding thereto but reacts specifically with given non-natural amino acid and tRNA* is necessary.

Thus, aaRS* having specificity to given non-natural amino acids, which is satisfactorily enhanced compared with specificity to existing natural amino acids, is used. This is because proteins into which natural amino acids have been introduced at sites into which given non-natural amino acids are to be introduced would be disadvantageously synthesized, otherwise. If aaRS* would react with tRNA that is inherent in the host cell besides tRNA*, non-natural amino acids would be introduced into sites into which natural amino acids should be introduced, besides sites into which non-natural amino acids are to be introduced. In order to avoid such problem, when prokaryotic cells are used as host cells, aaRS* that was constructed based on eukaryote-type aaRS may be used, because eukaryote-type aaRS is less likely to react with prokaryotic tRNA. The term "eukaryote-type aaRS" used herein refers to aaRS derived from eukaryotic organisms or aaRS derived from archaebacteria. If prokaryotic cells are used as host cells and prokaryote-derived aaRS* are introduced therein, such aaRS* may disadvantageously synthesize a plurality of types of aminoacyl tRNAs by recognizing tRNAs corresponding to natural amino acids inherent in the host cells as substrates, in addition to tRNA*. In such a case, unambiguous translation of a gene into a protein becomes difficult because of the aforementioned reasons. When prokaryotic host cells are used, accordingly, eukaryote-type aaRS* are to be used. When eukaryote-type cells are used as host cells, aaRS* prepared based on prokaryote-derived aaRS are used.

When alloproteins are synthesized, accordingly, adequate aaRS* needs to be prepared depending on whether the host cells to be used are eukaryotic or prokaryotic cells. aaRS* that can be used regardless of whether the host cells are eukaryote-type or prokaryotic cells rarely exists. When synthesis of alloproteins into which given non-natural amino acids have been incorporated is intended in eukaryote-type and prokaryotic cells, accordingly, preparation of prokaryote-derived aaRS* and eukaryote-type aaRS* is necessary. Preparation of aaRS*, however, requires modification of existing aaRS functions so as to realize activity of recognizing non-natural amino acids as substrates, which disadvantageously necessitates a large amount of labor.

Patent Document 1: WO 2003/014354
Patent Document 2: WO 2004/039989

DISCLOSURE OF THE INVENTION

Under the above circumstances, the present invention is intended to provide a method for producing alloproteins, which involves the use of either prokaryote-derived aaRS* or eukaryote-type aaRS* and which can use prokaryotic cells and eukaryote-type cells as host cells.

The method for producing alloproteins according to the present invention that has attained the above object comprises the following steps of:

(a) introducing genes encoding prokaryote-derived aminoacyl tRNA synthetase mutants having enhanced specificity to non-natural amino acids similar to given natural amino acids, compared with specificity to the natural amino acids, and tRNA genes for non-natural amino acids capable of binding to the non-natural amino acids in the presence of the prokaryote-derived aminoacyl tRNA synthetase mutants into prokaryotic cells that express genes encoding eukaryote-type aminoacyl tRNA synthetase having specificity to the given natural amino acids and tRNA genes capable of binding to the natural amino acids in the presence of the eukaryote-type aminoacyl tRNA synthetase;

(b) knocking out genes encoding aminoacyl tRNA synthetase having specificity to the natural amino acids, which are inherent in the prokaryotic cells, and inherent tRNA genes capable of binding to the natural amino acids in the presence of the inherent aminoacyl tRNA synthetase; and (c) expressing target proteins that are encoded by target genes having codons paired with anticodons of the tRNA genes for the non-natural amino acids in the prokaryotic cells.

According to the method for producing alloproteins of the present invention, the non-natural amino acids can be incorporated into codons paired with the anticodons to produce desired alloproteins in prokaryotic cells. Prokaryote-derived aminoacyl tRNA synthetase mutants that are used in the present invention are not limited to systems that synthesize alloproteins in prokaryotic cells. Such mutants can be applied to systems that synthesize alloproteins in eukaryotic cells.

Also, the method for producing alloproteins according to the present invention is not limited to systems involving the use of prokaryotic cells as host cells. Such method can be applied to systems involving the use of eukaryote-type aminoacyl tRNA synthetase mutants and eukaryote-type host cells.

The prokaryotic cells according to the present invention have the following properties:

(a) genes encoding eukaryote-type aminoacyl tRNA synthetase having specificity to given natural amino acids and tRNA genes capable of binding to the natural amino acids in the presence of the eukaryote-type aminoacyl tRNA synthetase have been introduced; and (b) genes encoding aminoacyl tRNA synthetase having specificity to the natural amino acids, which are inherent in the prokaryotic cells, and inherent tRNA genes capable of binding to the natural amino acids in the presence of the inherent aminoacyl tRNA synthetase have been knocked out.

The prokaryotic cells according to the present invention having such properties would use eukaryote-type aminoacyl tRNA synthetase and corresponding eukaryote-type tRNA, when incorporating natural amino acids similar to non-natural amino acids.

Further, the reagent kit for cell-free protein synthesis according to the present invention comprises at least the following elements:

(a) prokaryote-derived aminoacyl tRNA synthetase mutants having enhanced specificity to non-natural amino acids similar to given natural amino acids (compared with specificity to the natural amino acids);

(b) tRNA for non-natural amino acids capable of binding to the non-natural amino acids in the presence of the prokaryote-derived aminoacyl tRNA synthetase mutants;

(c) an amino acid solution comprising the non-natural amino acids; and (d) an extract of prokaryotic cells in which genes encoding eukaryote-type aminoacyl tRNA synthetase having specificity to the given natural amino acids and tRNA genes capable of binding to the natural amino acids in the presence of the inherent aminoacyl tRNA synthetase have been introduced and from which genes encoding aminoacyl tRNA synthetase having specificity to the natural amino acids, which are inherent in the prokaryotic cells, and inherent tRNA genes capable of binding to the natural amino acids in the presence of the inherent aminoacyl tRNA synthetase have been knocked out.

When such reagent kit for cell-free protein synthesis is used, eukaryote-type aminoacyl tRNA synthetase and corresponding eukaryote-type tRNA would be used, when incorporating natural amino acids similar to non-natural amino acids. The reagent kit for cell-free protein synthesis according to the present invention is not limited to systems involving the use of the aforementioned extract of prokaryotic cells. Such kit may be applied to systems involving the use of eukaryote-type aminoacyl tRNA synthetase mutants and the extract of eukaryotic cells.

This description includes part or all of the contents as disclosed in the description and/or drawings of Japanese Patent Application No. 2005-338402, which is a priority document of the present application.

BEST MODES FOR CARRYING OUT THE INVENTION

Figure 1:
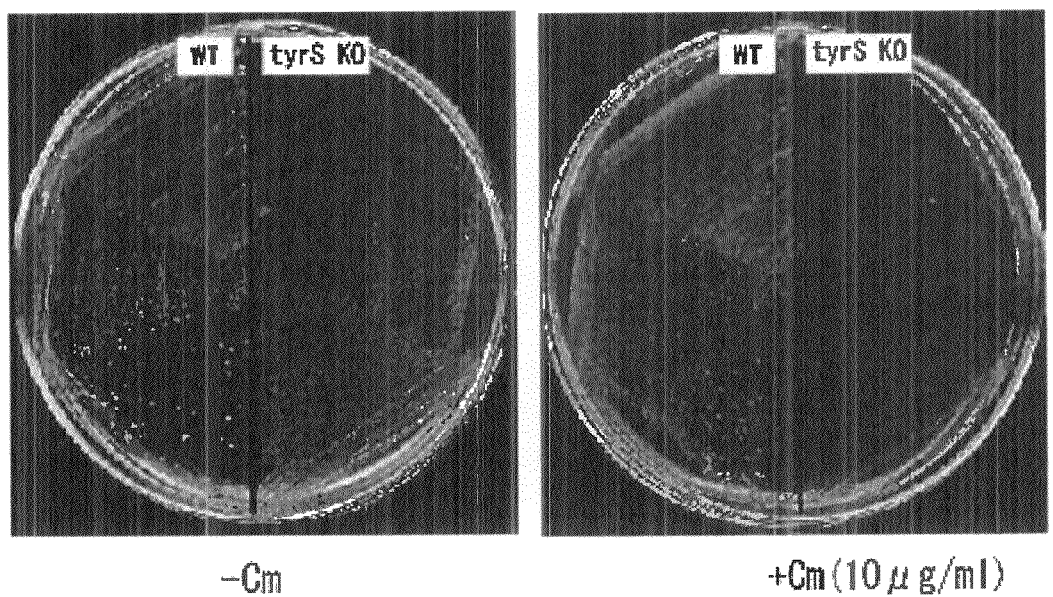
FIG. 1 is a photograph showing the results of transforming TOP10[ΔtyrU, ΔtyrS, pTK3] and TOP10 cells with the 2541supF plasmids and culturing the same in chloramphenicol-containing medium and chloramphenicol-free medium.

Hereafter, the present invention is described in greater detail.

The term "alloprotein" is defined as a protein into which non-natural amino acids have been incorporated. The method for producing proteins into which non-natural amino acids have been incorporated according to the present invention (hereafter referred to as a "method for producing alloproteins") involves the use of prokaryote-derived or eukaryote-type aminoacyl tRNA synthetase mutants (hereafter referred to as "aaRS*"). Regardless of a host cell type, i.e., prokaryotic cells, eukaryote-type cells, prokaryote-derived cell-free protein synthesis systems, or eukaryote-type cell-free protein synthesis systems, aaRS* can be applied to a wide variety of host cells.

In the present invention, the term "eukaryote-type" refers to both eukaryotes and archaebacteria. When it is described as "eukaryote-type aminoacyl tRNA synthetase," accordingly, such term refers to either eukaryote-type aminoacyl tRNA synthetase or archaebacteria-derived aminoacyl tRNA synthetase.

Non-Natural Amino Acids

In the present invention, the term "non-natural amino acids" refers to amino acids having structures different from those of 20 natural amino acid species. Since non-natural amino acids have structures similar to those of natural amino acids, non-natural amino acids are classified as derivatives or analogs of given natural amino acids. Examples of non-natural amino acids include derivatives of tyrosine that are natural amino acids, such as 3-substituted tyrosine and 4-substituted tyrosine. Examples of 3-substituted tyrosine include 3-halogenated tyrosine, such as 3-iodotyrosine and 3-bromotyrosine. Examples of 4-substituted tyrosine include 4-acetyl-L-phenylalanine, 4-benzoyl-L-phenylalanine, 4-azide-L-phenylalanine, O-methyl-tyrosine, and 4-iodo-L-phenylalanine.

Non-natural amino acids are not limited to tyrosine derivatives. Examples of non-natural amino acids include azidoalanine, azidohomoalanine, norleucine, norvaline, 4-aminotryptophan, 7-azatryptophan, 6-methyltryptophan, acetyllysine, ε-Boc-lysine, ε-methyllysine, 1-naphthylalanine, 2-naphthylalanine, styrylalanine, diphenylalanine, thiazolylalanine, 2-pyridylalanine, 3-pyridylalanine, 4-pyridylalanine, anthrylalanine, 2-amino-5-hexynoic acid, furylalanine, benzothienylalanine, thienylalanine, allylglycine, propargylglycine, phosphorylserine, phosphorylthreonine, and 2,3-diaminopropionic acid.

Aminoacyl tRNA Synthetase Mutants

In the present invention, "aaRS*" refers to mutant aminoacyl tRNA synthetase having enhanced specificity to non-natural amino acids similar to given natural amino acids, compared with specificity to the natural amino acids. When specificity is enhanced, an activity value regarding non-natural amino acids (i.e., the value obtained by dividing the reaction rate, $K_{cat}$, by the Michaelis constant, $K_m$) is significantly larger than the activity value regarding natural amino acids. The activity value can be measured by in vitro assay, and a relative activity value can be determined based on genetic data.

aaRS* thus defined can be obtained by introducing a mutation into a given site of known aminoacyl tRNA synthetase corresponding to natural amino acids. Known aminoacyl tRNA synthetase corresponding to natural amino acids first recognizes amino acids specifically, and it is activated with the addition of AMP, at the time of aminoacyl tRNA synthesis. Regarding known aminoacyl tRNA synthetase, a site that contributes to specific amino acid recognition is known, and such specificity can be changed by introducing a mutation into the relevant site. Based on such finding, a mutation that can reduce specificity to natural amino acids and enhance specificity to non-natural amino acids similar to the natural amino acids can be introduced. Thus, introduction of a mutation into a given site of known aminoacyl tRNA synthetase enables preparation of aaRS* having desired specificity.

Such aaRS* may be derived from prokaryotes or eukaryotes. An example of prokaryote-derived aaRS* is aaRS* (referred to as mutant TyrRS) having enhanced specificity to 3-iodo-L-tyrosine (i.e., a non-natural amino acid), compared with specificity to tyrosine (i.e., a natural amino acid). Mutant TyrRS is described in the following document. (Kiga, D., Sakamoto, K., Kodama, K., Kigawa, T., Matsuda, T., Yabuki, T., Shirouzu, M., Harada, Y., Naklayama, H., Takio, K., Hasegawa, Y., Endo, Y., Hirao, I. and Yokoyama, S., 2002, An engineered *Escherichia coli* tyrosyl-tRNA synthetase for site-specific incorporation of an unnatural amino acid into proteins in eukaryotic translation and its application in a wheat germ cell-free system, Proc. Natl. Acad. Sci. U.S.A., 99, 9715-9723)

According to this document, substitution of sites corresponding to tyrosine (Y) at position 37 and glutamine (Q) at position 195 in *E. coli*-derived tyrosyl-tRNA synthetase with other amino acid residues enables production of mutants having enhanced specificity to 3-halogenated tyrosine (non-natural amino acids). More preferably, mutants in which a position corresponding to tyrosine (Y) at position 37 is substituted with valine (V), leucine (L), isoleucine (I), or alanine (A) and a position corresponding to glutamine (Q) at position 195 is substituted with alanine (A), cysteine (C), serine (S), or asparagine (N) can be used. Such mutants have particularly enhanced specificity to 3-iodo-L-tyrosine.

Genes encoding such mutants can be easily prepared by known genetic engineering techniques. For example, genes encoding such mutants can be obtained by site-directed mutagenesis or with the use of a commercialized kit for site-directed mutagenesis.

Examples of other aaRS* derived from prokaryotes include those described in Chin, J. W., Cropp, T. A., Anderson, J. C., Mukherji, M., Zhang, Z., and Schlutz, P. G., 2003, An expanded eukaryotic genetic code. Science, 301, 964-967 and those described in Deiters, A., Cropp, T. A., Mukherji, M., Chin, J. W., Anderson, J. C., and Schultz, P. G, 2003, Adding amino acids with novel reactivity to the genetic codes of *Saccharomyces cerevisiae*. J. Am. Chem. Soc. 125, 11782-11783.

Examples of aaRS* derived from eukaryote-type include those described in Santoro, S. W., Wang, L., Herberich, B., King, D. S., Schultz, P. G.: An efficient system for the evolution of aminoacyl-tRNA synthetase specificity, Nature Biotechnol. 20, 1044-1048, 2002 and those described in Wang, L., Brock, A., Herberich, B., Schultz, P. G.: Expanding the genetic code of *Escherichia coli*, Science 292, 498-500, 2001.

tRNA Genes for Non-Natural Amino Acids

The term "tRNA genes for non-natural amino acids" refers to genes that encode tRNA, which is recognized by the aforementioned aaRS* and which has the 3' terminus to which activated non-natural amino acids are transferred. Specifically, such aaRS* has activity of recognizing given non-natural amino acids, synthesizing non-natural amino acids-AMP, and transferring the non-natural amino acids to the 3' terminus of tRNA for non-natural amino acids.

Here, tRNA for non-natural amino acids has an anticodon that is paired specifically with a genetic code other than the codons corresponding to 20 natural amino acid species. Preferably, an anticodon of tRNA for non-natural amino acids is composed of a sequence paired with a nonsense codon comprising an UAG amber codon, an UAA ochre codon, and an UGA opal codon. In other words, tRNA for non-natural amino acids is preferably nonsense suppressor tRNA. tRNA for non-natural amino acids having an anticodon paired with an UAG (i.e., an amber codon) is particularly preferable for the following reasons. That is, an opal codon may be sometimes translated into tryptophan at low efficiency, and such codon may be disadvantageously translated into two types of amino acids, i.e., non-natural amino acid and tryptophan. Thus, use of an opal codon is not adequate. Another reason is the presence of G as the third position of an amber codon. Nucleotide pairing of the third position of codon with the first position of anticodon is relatively unstable, and stable GC nucleotide pairing at this position is advantageous for suppressor tRNA to efficiently translate an UAG codon into a non-natural amino acid.

When a mutant of prokaryote-derived aaRS is used as the aforementioned aaRS*, the tRNA genes obtained from the same prokaryote can be used as the tRNA genes for non-natural amino acids. When the aforementioned *E. coli*-derived mutant TyrRS is used, use of the *E. coli*-derived suppressor tRNA gene is particularly preferable.

An anticodon of tRNA for non-natural amino acids is not limited to a sequence corresponding to a termination codon. Such anticodon may be composed of a sequence paired specifically with a codon comprising four or more nucleotides. Further, an anticodon of tRNA for non-natural amino acids may comprise non-natural nucleotides. In such a case, the other non-natural nucleotide that can form a nucleotide pair specifically with the non-natural nucleotide is introduced into a relevant site of the codon. Examples of pairs of such non-natural nucleotides include a pair of isoguanine and isocytidine and a pair of 2-amino-6-(2-thienyl)purine and pirydin-2-one.

Host Cells

Eukaryote-type or prokaryotic host cells may be used, regardless of whether the aforementioned aaRS* genes and tRNA genes for non-natural amino acids are derived from prokaryotes or of eukaryote-type.

When prokaryote-derived aaRS* genes and tRNA genes for non-natural amino acids are used and prokaryotic host cells are used, genes encoding aaRS having specificity to natural amino acid similar to the non-natural amino acid that serves as substrate for aaRS* (hereafter referred to as "corresponding aaRS gene inherent in prokaryotic cells") and tRNA genes capable of binding to natural amino acids in the presence of the corresponding aaRS gene inherent in prokaryotic cells (hereafter referred to as "corresponding tRNA genes inherent in prokaryotic cells") are substituted with eukaryote-type aaRS genes (hereafter referred to as "corresponding eukaryote-type aaRS genes") and tRNA genes (hereafter referred to as "corresponding eukaryote-type tRNA genes") in the prokaryotic cells.

When host cells are prokaryotic cells, more specifically, corresponding aaRS genes inherent in prokaryotic cells and corresponding tRNA genes inherent in prokaryotic cells are knocked out in the prokaryotic cells, and corresponding eukaryote-type aaRS genes and corresponding eukaryote-type tRNA genes are introduced into the prokaryotic cells. Prokaryote-derived aaRS* would selectively aminoacylate tRNA for non-natural amino acids without aminoacylating corresponding eukaryote-type tRNA. Also, corresponding eukaryote-type aaRS would selectively aminoacylate corresponding eukaryote-type tRNA without aminoacylating tRNA for non-natural amino acids.

When corresponding eukaryote-type aaRS genes and corresponding eukaryote-type tRNA genes are introduced into prokaryotic cells, expression vectors into which corresponding eukaryote-type aaRS genes and corresponding eukaryote-type tRNA genes have been expressibly introduced may be used, or such corresponding eukaryote-type aaRS genes and corresponding eukaryote-type tRNA genes may be expressibly introduced into the genomes of prokaryotic cells. Since genes that have been introduced can be expressed at high levels and alloproteins can be efficiently synthesized, use of expression vectors is preferable.

In the thus prepared prokaryotic cells, natural amino acids similar to target non-natural amino acids are incorporated into proteins with the aid of eukaryote-type aaRS and tRNA, so that alloproteins having target amino acid sequences can be properly synthesized.

Prokaryotic cells that can be used as host cells herein are not particularly limited. Examples thereof include *E. coli* and *Bacillus subtilis*.

When the aforementioned *E. coli*-derived mutant TyrRS is used, tyrosyl-tRNA synthetase derived from *Methanococcus jannaschii* can be used as eukaryote-type aaRS. *Methanococcus jannaschii*-derived tyrosyl-tRNA synthetase is composed of any protein selected from the group consisting of (a), (b), and (c):

(a) a protein comprising the amino acid sequence as shown in SEQ ID NO: 2;

(b) a protein comprising an amino acid sequence derived from the amino acid sequence as shown in SEQ ID NO: 2 by deletion, substitution, or addition of one or several amino acids and having activity of activating tyrosine and synthesizing tyrosyl tRNA; and (c) a protein encoded by a polynucleotide hybridizing under stringent conditions to a complementary strand of the polynucleotide encoding a protein comprising the amino acid sequence as shown in SEQ ID NO: 2 and having activity of activating tyrosine and synthesizing tyrosyl tRNA.

When the aforementioned *E. coli*-derived mutant TyrRS is used, *Methanococcus jannaschii*-derived tyrosine tRNA genes can be used as eukaryote-type tRNAs. *Methanococcus jannaschii*-derived tyrosine tRNA is composed of any polynucleotide selected from the group consisting of (a), (b), and (c) below:

(a) a polynucleotide consisting of nucleotides 4334 to 4410 of SEQ ID NO: 1;

(b) a polynucleotide comprising a nucleotide sequence derived from the sequence consisting of nucleotides 4334 to 4410 of SEQ ID NO: 1 by deletion, substitution, or addition of one or more nucleotides and capable of binding activated tyrosine in the presence of *Methanococcus jannaschii*-derived tyrosyl-tRNA synthetase; and (c) a polynucleotide hybridizing under stringent conditions to a complementary strand of a polynucleotide consisting of nucleotides 4334 to 4410 of SEQ ID NO: 1 and capable of binding activated tyrosine in the presence of *Methanococcus jannaschii*-derived tyrosyl-tRNA synthetase.

Under stringent conditions, specific hybridization takes place but nonspecific hybridization does not take place. For example, hybridization may be carried out using 6× SSC buffer (0.9M NaCl, 0.09M sodium citrate) and at 55° C.

When prokaryote-derived aaRS* genes and tRNA genes for non-natural amino acids are used and eukaryote-type cells are used as host cells, aaRS specific to natural amino acids inherent in the eukaryote-type cells and tRNA genes capable of binding to natural amino acids in the presence of the aaRS can be used without substitution. In such a case, eukaryote-type host cells can be used remaining unchanged.

Eukaryote-type cells that can be used as host cells are not particularly limited. Examples thereof include eukaryotic cells, such as yeast, plant, insect, and mammalian cells, and archaebacteria cells. Mammalian cells are particularly preferable since the gene recombinant systems thereof have been established. Examples of useful mammalian cells include Chinese hamster ovary (CHO) cells and COS cells. Specific examples include SV40-transformed monkey kidney cells CV1 (COS-7), human embryonic kidney cells (293 cells), Chinese hamster ovary/-DHFR cells, mouse Sertoli cells (TM4), human pneumocytes (W138), human liver cells (Hep G2), and mouse breast cancer cells (MMT060562).

When eukaryote-type aaRS* genes and tRNA genes for non-natural amino acids are used and eukaryote-type cells are used as host cells, genes encoding aaRS having specificity to natural amino acids similar to non-natural amino acids that serve as substrates for aaRS* (hereafter referred to as "corresponding aaRS genes inherent in eukaryotes") and tRNA genes capable of binding to natural amino acids in the presence of the corresponding aaRS genes inherent in eukaryotes (hereafter referred to as "corresponding tRNA genes inherent in eukaryotes") are substituted with prokaryote-derived aaRS genes (hereafter referred to as "corresponding prokaryote-derived aaRS genes") and tRNA genes (hereafter referred to as "corresponding prokaryote-derived tRNA genes") in the eukaryote-type cells.

When host cells are eukaryote-type cells, more specifically, corresponding aaRS genes inherent in eukaryotes and corresponding tRNA genes inherent in eukaryotes are knocked out in the eukaryote-type cells, and corresponding prokaryote-derived aaRS genes and corresponding prokaryote-derived tRNA genes are introduced into the eukaryote-type cells. Eukaryote-type aaRS* would selectively aminoacylate tRNA for non-natural amino acids without aminoacylating corresponding prokaryote-derived tRNA. Also, corresponding prokaryote-derived aaRS would selectively aminoacylate corresponding prokaryote-derived tRNA without aminoacylating tRNA for non-natural amino acids.

When corresponding prokaryote-derived aaRS genes and corresponding prokaryote-derived tRNA genes are introduced into eukaryote-type cells, expression vectors into which corresponding prokaryote-derived aaRS genes and corresponding prokaryote-derived tRNA genes have been expressibly introduced may be used, or such corresponding prokaryote-derived aaRS genes and corresponding prokaryote-derived tRNA genes may be expressibly introduced into the genomes of eukaryote-type cells. Since genes that have been introduced can be expressed at high levels and alloproteins can be efficiently synthesized, use of expression vectors is preferable.

In the thus prepared eukaryote-type cells, natural amino acids similar to target non-natural amino acids are incorporated into proteins with the aid of prokaryote-derived aaRS and tRNA, so that alloproteins having target amino acid sequences can be properly synthesized.

When eukaryote-type aaRS* genes and tRNA genes for non-natural amino acids are used and prokaryotic cells are used as host cells, aaRS specific to natural amino acids inherent in the prokaryotic cells and tRNA genes capable of binding to natural amino acids in the presence of the aaRS can be used without substitution. In such a case, prokaryotic host cells can be used remaining unchanged.

Target Protein and Method for Producing the Same

The aforementioned aaRS* genes, tRNA genes for non-natural amino acids, and host cells can be used to prepare target proteins (i.e., alloproteins) into which non-natural amino acids have been incorporated. Target proteins are not particularly limited, provided that sequences thereof comprise codons at desired sites, which are paired with anticodons of the aforementioned tRNA for non-natural amino acids of the genes encoding the target proteins. Thus, alloproteins having non-natural amino acids at desired sites can be prepared. Specifically, desired sites of wild-type genes may be mutated into sequences that are paired with anticodons of tRNA for non-natural amino acids via site-directed mutagenesis to prepare genes encoding alloproteins.

The resulting genes encoding the target proteins are introduced into host cells by a conventional technique and expressed therein. In host cells, alloproteins into which non-natural amino acids have been incorporated at sites of codons paired with anticodons of tRNA for non-natural amino acids of the above genes can be synthesized.

Target proteins (i.e., alloproteins) are not particularly limited. Examples thereof include a group of proteins associated with cell signaling (e.g., epidermal growth factor receptors, nerve growth factor receptors, Grab2 proteins, Src kinase, and Ras proteins), a group of proteins associated with translation (e.g., polypeptide elongation factors, initiating factors, transcription termination factors, ribosome proteins, and aminoacyl tRNA synthetase), transcription factors, and membrane proteins.

The prepared alloproteins can be used for (i) structure determination via X-ray crystallographic analysis, (ii) photocrosslinking or site-directed fluorescent labeling for elucidation of cell signaling pathways, (iii) use as a proteinous drug upon site-directed polyethyleneglycolation for enhancing drug efficacy, and other purposes. According to protein function analysis via site-directed amino acid substitution, amino acids that can be used for substitution are limited to 20 natural amino acid species in the past. Use of non-natural amino acids enables amino acid substitution with a wide variety of amino acid residues without limitation. Thus, analysis of prepared mutants enables elucidation of roles of amino acid residues at specific sites in proteins.

Reagent Kit for Cell-Free Protein Synthesis aaRS* and tRNA for non-natural amino acids described above can be used as part of a so-called "reagent kit for cell-free protein synthesis." In general, a reagent kit for cell-free protein synthesis comprises various cell extracts while maintaining the protein synthesis capacities. In cell-free protein synthesis systems, translation systems and transcription/translation systems are known. With the addition of mRNA or DNA encoding a target protein to the reaction solution, proteins are synthesized with the aid of activities of various enzymes contained in extracts.

The reagent kit for cell-free protein synthesis according to the present invention comprises at least an amino acid solution comprising non-natural amino acids similar to given natural amino acids, a set of aaRS* and tRNA for non-natural amino acids described above, and extracts of host cells. The reagent kit for cell-free protein synthesis according to the present invention may further comprise a solution of vector DNA that can incorporate genes encoding target proteins therein and a set of reagents comprising RNA polymerase for transcribing genes encoding target proteins, which are included in general, commercially available, and known reagent kit for cell-free protein synthesis.

In the reagent kit for cell-free protein synthesis according to the present invention, the extracts of host cells may be of either eukaryote-type or prokaryotic cells. When prokaryote-derived aaRS* and an extract of prokaryotic cells are used, however, extracts of prokaryotic cells in which the aforementioned "corresponding aaRS genes inherent in prokaryotic cells" and from which "corresponding tRNA genes inherent in prokaryotic cells" have been knocked out, and the "corresponding eukaryote-type aaRS genes" and "corresponding eukaryote-type tRNA genes" have been introduced should be used. In such a case, "aaRS* genes" and "tRNA genes for non-natural amino acids" may further be introduced into prokaryotic cells, or "aaRS*" and "tRNA for non-natural amino acids" are added to the culture solution of prokaryotic cells remaining unchanged, so as to incorporate "aaRS*" and "tRNA for non-natural amino acids" into the extract of prokaryotic cells.

When prokaryote-derived aaRS* and an extract of eukaryote-type cells are used for the reagent kit for cell-free protein synthesis according to the present invention, also, aaRS specific to natural amino acids inherent in the eukaryote-type cells and tRNA genes capable of binding to natural amino acids in the presence of aaRS can be used without substitution. In such a case, an extract of wild-type eukaryote-type cells can be used remaining unchanged.

When eukaryote-type aaRS* and an extract of eukaryote-type cells are used for the reagent kit for cell-free protein synthesis according to the present invention, an extract of eukaryote-type cells in which the "corresponding aaRS genes inherent in eukaryotes" and from which the "corresponding tRNA genes inherent in eukaryotes" have been knocked out is used. In such a case, the "corresponding prokaryote-derived aaRS genes" and the "corresponding prokaryote-derived tRNA genes" may be introduced into eukaryote-type cells, and the "corresponding prokaryote-derived aaRS" and "corresponding prokaryote-derived tRNA" can thus be incorporated into the extract of eukaryote-type cells. Alternatively, products of "corresponding prokaryote-derived aaRS genes" and "corresponding prokaryote-derived tRNA genes" may be added to extracts.

When eukaryote-type aaRS* and an extract of prokaryotic cells are used for the reagent kit for cell-free protein synthesis according to the present invention, aaRS specific to natural amino acids inherent in the prokaryotic cells and tRNA genes capable of binding to natural amino acids in the presence of the aaRS can be used without substitution. In such a case, extracts of wild-type prokaryotic cells can be used remaining unchanged.

Hereafter, the present invention is described in greater detail with reference to the examples, although the technical scope of the present invention is not limited thereto.

EXAMPLE 1

In this example, a method for producing alloproteins wherein *E. coli*-derived aaRS* (i.e., mutant TyrRS having enhanced specificity to 3-iodo-L-tyrosine compared with specificity to tyrosine) was used, and *E. coli* host cells were used was examined.

At the outset, mutant TyrRS genes and suppressor tRNA$^{Tyr}$ genes were prepared in the following manner.

Mutant TyrRS

*E. coli* TyrRS genes were isolated from *E. coli* chromosomes and then subjected to cloning. The cloned genes were then subjected to amino acid substitution, i.e., from tyrosine to valine (position 37) and from asparagine to cysteine (position 195), so as to prepare mutant TyrRS genes having enhanced specificity to 3-iodo-L-tyrosine compared with specificity to tyrosine. Preparation of *E. coli* chromosomes, isolation of genes of interest from the chromosomes via a gene amplification technique (i.e., PCR), and cloning of the isolated genes into adequate vectors can be easily performed via known gene engineering techniques. In order to express mutant TyrRS genes, promoters originating from TyrRS genes may be subjected to isolation and cloning together with TyrRS structural genes. A specific example of a vector that can be used is a vector originating from the pBR322 plasmid.

Suppressor tRNA$^{Tyr}$

A full-length of a gene of small-sized RNA such as tRNA can be prepared via a chemical technique. The nucleotide sequence of the suppressor tRNA$^{Tyr}$ gene is GGTGGGGT-TCCCGAGCGGCCAAAGGGAGCA-GACTCTAAATCTGCCGTCATCGA CTTCGAAGGTTC-GAATCCTTCCCCCACCACCA. A transcription promoter originating from the 1 pp gene was isolated from the *E. coli* chromosome and ligated to a site in front of the gene of interest. A transcription termination sequence originating from the rrnC gene that had been prepared via chemical synthesis was ligated to a site behind the gene of interest. The full-length nucleotide sequence after ligation is represented by: GCATGCGGCGCCGCTTCTTTGAGCGAAC-GATCAAAAATAAGTGGCGCCCATC AAAAAAATAT-TCTCAACATAAAAAACTTTGTG-TAATACTTGTAACGCTGCCATC AGACGCATTGGTGGGGTTCCCGAGCGGC-CAAAGGGAGCAGACTCTAAATCTGC CGTCATC-GACTTCGAAGGTTCGAATCCTTC-CCCCACCACCATTTATCACAGATTG GAAATTTTTGATCCTTAGC-GAAAGCTAAGGATTTTTTTTAGTCGAC. This nucleotide sequence was cloned into a vector originating from pBR322 together with the mutant TyrRS gene.

pEcIYRS Plasmid

The plasmids comprising the mutant TyrRS genes and the suppressor tRNA$^{Tyr}$ genes prepared above were designated as "pEcIYRS." In *E. coli* cells into which such plasmids had been introduced, the mutant TyrRS genes are constitutively expressed from the own transcription promoter region, and the suppressor tRNA genes are constitutively expressed from the 1 pp promoter region.

Construction of "Corresponding Eukaryote-Type aaRS" and "Corresponding Eukaryote-Type tRNA" Expression Plasmids In this example, archaebacteria *Methanococcus jannaschii*-derived TyrRS and tyrosine tRNA were expressed in host cells as "corresponding eukaryote-type aaRS" and "corresponding eukaryote-type tRNA." The pTK3 plasmid expressing *Methanococcus jannaschii*-derived TyrRS genes and tyrosine tRNA genes was constructed in the following manner. The full-length nucleotide sequence of the pTK3 plasmid is shown in SEQ ID NO: 1. The TyrRS gene of archaebacteria *Methanococcus jannaschii* is composed of the sequence consisting of nucleotides 3284 to 4204 of SEQ ID NO: 1. The amino acid sequence of TyrRS derived from archaebacteria *Methanococcus jannaschii* is shown in SEQ ID NO: 2. The tyrosine tRNA gene of archaebacteria *Methanococcus jannaschii* is composed of the sequence consisting of nucleotides 4410 to 4334 in SEQ ID NO: 1. Further, the kanamycin-resistant gene included in the pTK3 plasmid is composed of the sequence consisting of nucleotides 4847 to 5662 in SEQ ID NO: 1. The amino acid sequence of the protein encoded by the kanamycin-resistant gene is shown in SEQ ID NO: 3.

A method for constructing the pTK3 plasmid is summarized as follows. A promoter region of the TrpRS gene was isolated from the *E. coli* chromosome via PCR and cloned into the pACYC184 vector. The plasmid was designated as pPTRP. The TyrRS gene of *Methanococcus jannaschii* was isolated from the chromosome thereof via PCR, and cloned into a site immediately behind the TrpRS promoter region of the pPTRP plasmid to prepare the pMjYS plasmid. Preparation of *E. coli* chromosomes, isolation of genes of interest from the chromosomes via a gene amplification technique (i.e., PCR), and cloning of the isolated genes into adequate plasmids can be easily performed via known gene engineering techniques. The full-length of the tyrosine tRNA gene of *Methanococcus jannaschii* was prepared via a chemical technique. A transcription promoter originating from the 1 pp gene was isolated from the *E. coli* chromosome and ligated to a site in front of the gene of interest. A transcription termination sequence originating from the rrnC gene that had been prepared via chemical synthesis was ligated to a site behind the gene of interest. The resultant was cloned into the pMjYS plasmid to prepare the pMjYRS plasmid. The kanamycin-resistant gene that had been cloned into the commercially available pHSG299 plasmid (Takara Shuzo Co., Ltd.) was prepared, extracted via PCR, and cloned into the pMjYRS plasmid to prepare the pTK3 plasmid.

The thus-obtained pTK3 plasmid was used to transform the *E. coli* TOP10 cell. The TOP10 cell that has been subjected to treatment which is suitable for electroporation-based transformation was used (commercially available from Invitrogen).

Knockout of "Corresponding Prokaryote-Derived aaRS" and "Corresponding Prokaryote-Derived tRNA"

In this example, tyrosyl-tRNA synthetase genes (tyrS genes) and tyrosine tRNA genes (tyrT genes and tyrU genes) in the *E. coli* TOP10 host cells were knocked out.

In this example, the Quick and easy BAC modification kit (hereafter abbreviated as "QBM" kit, Gene Bridges) was used to knockout tyrS genes, tyrT genes, and tyrU genes in the TOP 10 cells that had been transformed by the pTK3 plasmid. The order for knocking out the genes was not limited to the order described in the examples, provided that the genes would be knocked out in the end. The QBM kit is intended to manipulate bacterial artificial chromosomes (BAC), and it can be used for knocking out the genes in the *E. coli* chromosomes. The experimental procedure was in accordance with the instructions of the kit. Specifically, two nucleotide sequences each comprising about 50 nucleotides that are located adjacent to the gene x (i.e., the tyrS, tyrT, or tyrU gene, which is to be removed from the chromosome) in the chromosome are designated as x-L and x-R. By amplifying the marker gene via PCR with the use of a pair of primers having x-L and x-R, DNA comprising x-L and x-R ligated to both sides of the marker gene can be obtained. When such DNA is knocked in to the chromosome using the QBM kit, *E. coli* in which the gene x has been substituted with the marker gene can be obtained.

In view of removal of the marker gene knocked in to the chromosome, use of the chloramphenicol-resistant gene (i.e., the CAT gene) instead of the ampicillin-resistant gene or kanamycin-resistant gene is preferable as the marker gene. In this example, the CAT gene was used as the marker gene.

(1) Knockout of tyrS Gene

In order to knock out the tyrS gene, tyrS-L and tyrS-R were determined as x-L and x-R above.

```
tyrS-L:
                                         (SEQ ID NO: 4)
ATGCGTGGAAGATTGATCGTCTTGCACCCTGAAAAGATGCAAAAATCTTG tyrS-R:
                                         (SEQ ID NO: 5)
ACAGGGAACATGATGAAAAATATTCTCGCTATCCAGTCTCACGTTGTTTA
``` tyrSL-CmF and tyrSR-CmR1 were designed as a tyrS-L-containing primer and a tyrS-R-containing primer, and these primers were prepared via chemical synthesis.

```
tyrSL-CmF (70 nucleotides):
                                         (SEQ ID NO: 6)
ATGCGTGGAAGATTGATCGTCTTGCACCCTGAAAAGATGCAAAAATCTT

GACCCGACGCACTTTGCGCCG tyrSR-CmR1 (71 nucleotides):
                                         (SEQ ID NO: 7)
TAAACAACGTGAGACTGGATAGCGAGAATATTTTTCATCATGTTCCCTG

TTTACGCCCCGCCCTGCCACTC
```

PCR was carried out using tyrSL-CmF and tyrSR-CmR1 and the pACYC184 vector as a template to amplify a DNA fragment containing the CAT gene comprising tyrS-L and tyrS-R ligated to both ends thereof. SEQ ID NO: 16 shows the nucleotide sequence of the CAT gene. In this example, the CAT gene that comprises a transcription promoter sequence and the Shine-Dalgarno sequence (the SD sequence) but does not comprise a transcription termination sequence was used. The transcription promoter and the SD sequence enable expression of the CAT gene. Since the transcriptional promoter of the pdxY gene located downstream of the tyrS gene is present inside the tyrS gene, a knockout of the tyrS gene would disadvantageously quench pdxY gene expression. By refraining from incorporating a transcription termination sequence into the CAT gene to be introduced, accordingly, the pdxY gene can be coexpressed with the CAT gene.

Subsequently, the thus-amplified DNA fragment was knocked in to the chromosome of the E. coli TOP10 cell using the QBM kit. The CAT gene that had been knocked in to the chromosome would comprise at its both ends tyrS-L and tyrS-R. Accordingly, knock-in of a DNA fragment comprising tyrS-L and tyrS-R directly ligated with each other to the chromosome with the use of the QBM kit enables removal of the CAT gene from the chromosome. If a DNA fragment comprising tyrS-L and tyrS-R directly ligated with each other is properly knocked in to the chromosome, more specifically, the E. coli TOP10 cell becomes sensitive to chloramphenicol (Cm).

The efficiency of proper knock-in with the use of the QBM kit is 1/10,000 or lower. Accordingly, Cm-sensitive E. coli cells were selected in accordance with the following procedure. At the outset, the amplified DNA fragment was introduced, and 1 to 100,000 E. coli cells were cultured in liquid LB medium. When the number of E. coli cells reached 100,000 to 1,000,000 cells/ml via culture, 10 μg/ml Cm was added to the medium, and culture was then continued. Thirty minutes later, 200 μg/ml ampicillin was added to the medium, and culture was continued for about 30 minutes to 1 hour until E. coli cells were lysed. Subsequently, the lysed culture solution was centrifuged, precipitated E. coli cells were inoculated onto an LB plate, and culture was then carried out overnight. One hundred to two hundreds of resulting colonies were selected and Cm-sensitive cells were selected therefrom via the replica method.

Thus, the tyrS genes were knocked out from chromosomes of the E. coli TOP10 cells.

(2) Knockout of tyrT Genes

In the same manner as in "(1) Knockout of tyrS gene" above, the tyrT gene, which is a tyrosine tRNA gene, was knocked out from the E. coli TOP10 cell. In this case, tyrT-L and tyrT-R were determined as x-L and x-R, respectively.

```
tyrT-L:
                                         (SEQ ID NO: 8)
AAAATAACTGGTTACCTTTAATCCGTTACGGATGAAAATTACGCAACCAG tyrT-R:
                                         (SEQ ID NO: 9)
AGTCCCTGAACTTCCCAACGAATCCGCAATTAAATATTCTGCCCATGCGG
``` tyrTL-CmF and tyrTR-CmR1 were designed as a pair of primers used for PCR involving the use of the CAT gene of the pACYC184 vector as a template and the primers were chemically synthesized.

```
tyrTL-CmF (70 nucleotides):
                                        (SEQ ID NO: 10)
AAAATAACTGGTTACCTTTAATCCGTTACGGATGAAAATTACGCAACCA

GACCCGACGCACTTTGCGCCG tyrTR-CmR1 (71 nucleotides):
                                        (SEQ ID NO: 11)
CCGCATGGGCAGAATATTTAATTGCGGATTCGTTGGGAAGTTCAGGGAC

TTTACGCCCCGCCCTGCCACTC
```

In this example, the CAT gene included in the PCR-amplified DNA fragment that comprises a transcription promoter sequence and the Shine-Dalgarno sequence (the SD sequence) but does not comprise a transcription termination sequence was used. The tpr gene located downstream of the tyrT gene can be coexpressed with the CAT gene. With the amplified DNA fragment knocked in to the chromosome of the E. coli TOP10 cells with the use of the QBM kit and the CAT gene then removed in a similar manner, the tyrT gene was successfully knocked out.

(3) Knockout of tyrU Genes

In the same manner as in "(1) Knockout of tyrS gene" above, the tyrU gene, which is a tyrosine tRNA gene, was knocked out from the E. coli TOP10 cell. In this case, tyrU-L and tyrU-R were determined as x-L and x-R, respectively.

```
tyrU-L:
                                        (SEQ ID NO: 12)
GTAATCAGTAGGTCACCAGTTCGATTCCGGTAGTCGGCACCATCAAGTCC tyrU-R:
                                        (SEQ ID NO: 13)
GGCCACGCGATGGCGTAGCCCGAGACGATAAGTTCGCTTACCGGCTCGAA
``` tyrUL-CmF and tyrUR-CmR1 were designed as a pair of primers used for PCR involving the use of the CAT gene of the pACYC184 vector as a template, and the primers were chemically synthesized.

```
tyrUL-CmF1 (72 nucleotides):
                                          (SEQ ID NO: 14)
GTAATCAGTAGGTCACCAGTTCGATTCCGGTAGTCGGCACCATCAAGTC

CGATTTTCAGGAGCTAAGGAAGC tyrUR-CmR1 (71 nucleotides):
                                          (SEQ ID NO: 15)
TTCGAGCCGGTAAGCGAACTTATCGTCTCGGGCTACGCCATCGCGTGGC

CTTACGCCCCGCCCTGCCACTC
```

In this example, the CAT gene included in the PCR-amplified DNA fragment that comprises the SD sequence but does not comprise a transcription termination sequence or a transcription promoter sequence was used. The tyrU genes are cotranscribed with its upstream thrU gene and downstream glyT gene, and a transcription promoter is not necessary at a site upstream of the CAT gene. If the SD sequence for translation is present, expression of the CAT gene becomes possible. By refraining from incorporating a transcription termination sequence into the CAT gene to be introduced, the glyT gene can be coexpressed with the CAT gene. After the amplified DNA fragment was knocked in to the chromosome of the E. coli TOP10 cells with the use of the QBM kit, the tyrU gene was knocked out by removing the CAT gene in a similar manner.

SEQ ID NO: 16 shows the nucleotide sequence of the CAT gene that comprises the transcription promoter sequence and the SD sequence but does not comprise a transcription termination sequence, which was used for knocking out tyrS gene and tyrT gene. SEQ ID NO: 17 shows the nucleotide sequence of the CAT gene that comprises the SD sequence but does not comprise a transcription promoter sequence or transcription termination sequence, which was used for knocking out the tyrU gene.

Preparation of Alloprotein

In the E. coli TOP10 cells, which were obtained by introducing the pTK3 plasmid therein and knocking out the tyrS, tyrT, and tyrU genes in the above-described manner (hereafter referred to as "TOP10*" or "TOP10[ΔtyrT, ΔtyrU, ΔtyrS, pTK3] cells"), tyrosine would be incorporated into a tyrosine-encoding site of genes expressed therein with the aid of archaebacteria Methanococcus jannaschii TyrRS and tyrosine tRNA. Thus, introduction of the pEcIYRS plasmid that expresses mutant TyrRS and suppressor tyrosine tRNA having enhanced specificity to 3-iodo-L-tyrosine compared with specificity to tyrosine into the TOP10* cells would result in synthesis of alloproteins comprising 3-iodotyrosine incorporated into the site of an amber codon paired with an anticodon of suppressor tRNA$^{Tyr}$. Tyrosine would be incorporated into the site of a codon encoding tyrosine in the gene encoding the introduced protein of interest as with the case of other genes, with the aid of archaebacteria Methanococcus jannaschii TyrRS and tyrosine tRNA.

In such a case, mutant TyrRS, which is prokaryote-derived aaRS*, would not arainoacylate Methanococcus jannaschii-derived tRNA, and Methanococcus jannaschii TyrRS would not aminoacylate suppressor tRNA$^{Tyr}$. With the use of the E. coli TOP10 cells into which the pEcIYRS plasmid has been introduced, accordingly, alloproteins comprising non-natural amino acids, i.e., 3-iodotyrosine, incorporated selectively into desired positions can be synthesized. This can be verified by an experiment described below.

This experiment involves the use of an amber mutant gene (SEQ ID NO: 18) of glutathione-S-transferase (hereafter referred to as "GST") comprising an amber codon introduced into the coding sequence. In this amber mutant gene of GST, the 25th codon from the N terminus is substituted with an amber codon. With the use of a peptide obtained by treating a GST protein with trypsin, a peptide containing such site can be easily detected via mass analysis. This enables identification of whether or not an amino acid at this site is iodotyrosine. The amber mutant gene of GST may be ligated to an adequate expression promoter and cloned into pEcIYRS. Thus, such gene can be expressed in E. coli. An example of an adequate promoter is lacZ-UV5 promoter. The pEcIYRS plasmid into which the amber mutant gene of GST has been cloned is designated as the pEcIYRS-GST(Am) plasmid.

The pEcIYRS-GST(Am) plasmid is introduced into the TOP10* cells in the following manner. TOP10* cells are inoculated into 1.5 ml of liquid LB medium, cultured therein, and allowed to grow to a concentration of about 1,000,000 cells/ml. The culture solution is then recovered, and centrifugation is carried out at 4° C. and 11.000 rpm for 30 seconds to precipitate the cells. The supernatant is discarded, and the precipitate is then suspended in 1 ml of ice-cooled sterilized water. The suspension is subjected to centrifugation again at 4° C. and 11,000 rpm for 30 seconds to precipitate the cells, the supernatant is discarded, and the precipitate is then suspended in 1 ml of ice-cooled sterilized water again. Finally, cells are precipitated via centrifugation at 4° C. and 11,000 rpm for 30 seconds and then suspended in 20 to 30 μl of sterilized water. Thus, TOP10* cells suitable for electroporation are prepared. The pEcIYRS-GST(Am) plasmid is introduced therein by the same manner, so as to prepare TOP10* [pEcIYRS-GST(Am)].

In order to prepare GST into which 3-iodo-L-tyrosine are introduced at position 25, TOP10*[pEcIYRS-GST(Am)] is cultured in liquid LB medium containing 0.1 mg/ml 3-iodo-L-tyrosine and 0.1 mg/ml ampicillin. In order to induce expression of the GST(Am) gene, isopropyl-1-thio-β-D-galactoside (IPTG) is added to a medium to result in a final concentration of 1 mM. The cells are recovered several hours after the addition of IPTG, an E. coli extract is prepared by a known technique, and GST is then purified using a GST affinity column (Amersham). The obtained GST may be analyzed via mass analysis to confirm that iodo tyrosine has been introduced into a predetermined position 25 and that other tyrosine codons have been translated into tyrosine.

Experimentation and Result-1

In accordance with the description above, substituted E. coli cells that can be used as host cells for production of alloproteins involving the use of E. coli-derived mutant TyrRS genes and suppressor tRNA$^{Tyr}$ genes were prepared.

More specifically, the pTK3 plasmid that expresses the Methanococcus jannaschii-derived TyrRS gene and the tyrosine tRNA gene was first transformed into the E. coli TOP10 cell, in accordance with the description above. Thereafter, a mutant was prepared in accordance with the description above by knocking out the tyrS gene in the pTK3-containing E. coli TOP10 cell (TOP10[pTK3] cell) (i.e., TOP10 [ΔtyrS, pTK3] cell). Further, a mutant was prepared in accordance with the description above by knocking out the tyrU gene in the mutant (TOP10[ΔtyrS, pTK3] cell) (i.e., TOP10[ΔtyrU, ΔtyrS, pTK3] cell).

An amber suppression test was carried out to verify that the tyrS gene has been knocked out in the resulting TOP10 [ΔtyrU, ΔtyrS, pTK3] cell. The 2541supF plasmid was prepared for this test. The amber mutant chloramphenicol-resistant gene and the E. coli tyrosine tRNA-derived amber suppressor tRNA gene have been cloned into the 2541supF plasmid. SEQ ID NO: 19 shows the full-length nucleotide sequence of the 2541supF plasmid.

If the *E. coli* TyrRS (i.e., the tyrS gene product) is expressed in the *E. coli* cell into which the 2541supF plasmid has been introduced, suppressor tRNA that is present in the 2541 supF plasmid would function, which in turn would suppress amber mutation and express chloramphenicol resistance. If *E. coli* TyrRS (i.e., the tyrS gene product) is knocked out in the *E. coli* cell into which the 2541 supF plasmid has been introduced, it is deduced that chloramphenicol resistance would not be expressed. Since suppressor tRNA in the 2541 supF plasmid would not be recognized by archaebacteria-derived TyrRS, chloramphenicol resistance would not be expressed even if archaebacteria-derived TyrRS has been expressed in the *E. coli* cell into which the 2541supF plasmid has been introduced.

FIG. 1 shows the results of transforming TOP10[ΔtyrU, ΔtyrS, pTK3] and wild-type TOP10 cells with the 2541supF plasmids and then culturing the same in a chloramphenicol-containing medium. As shown in FIG. 1, the TOP10 cell (shown as "WT") transformed by the 2541supF plasmid grew on a chloramphenicol (Cm)-containing medium. The TOP10 [ΔtyrU, ΔtyrS, pTK3] cells (shown as "tyrS KO"), however, did not grow on a Cm-containing medium. These results indicate that *E. coli* TyrRS has not been expressed in the TOP10[ΔtyrU, ΔtyrS, pTK3] cells.

Experimentation and Result-2

The tyrT gene was knocked out in the TOP10[ΔtyrU, ΔtyrS, pTK3] cell, in which complete knockout of TyrRS inherent in *E. coli* had been confirmed, in accordance with the above-described manner to construct mutants (TOP10[ΔtyrT, ΔtyrU, ΔtyrS, pTK3] cells).

Whether or not all tyrosine tRNAs inherent in *E. coli* had been knocked out in the prepared mutants was examined in the following manner.

Specifically, *E. coli* TyrRS mutants were first expressed in the TOP10[ΔtyrT, ΔtyrU, ΔtyrS, pTK3] cells. The mutants described in the document (Kiga, D. et al., 2002, Proc. Natl. Acad. Sci. USA 99, 9715-9723) were used. The *E. coli* TyrRS mutants are capable of recognizing 3-iodotyrosine (or 3-bromotyrosine) and binding the same to *E. coli* tyrosine tRNA. When *E. coli* cells in which such mutants have been expressed are inoculated into a bromotyrosine-containing medium, accordingly, bromotyrosine would be incorporated into all proteins instead of tyrosin in such *E. coli* cells. When *E. coli* TyrRS mutants function and *E. coli* tyrosine tRNA are present, accordingly, no protein would function, and *E. coli* cell cannot grow. When *E. coli* TyrRS mutants function but *E. coli* tyrosine tRNA is not present in *E. coli*, however, *E. coli* cells can grow on a bromotyrosine-containing medium even if *E. coli* TyrRS mutants would function.

Figure 2:
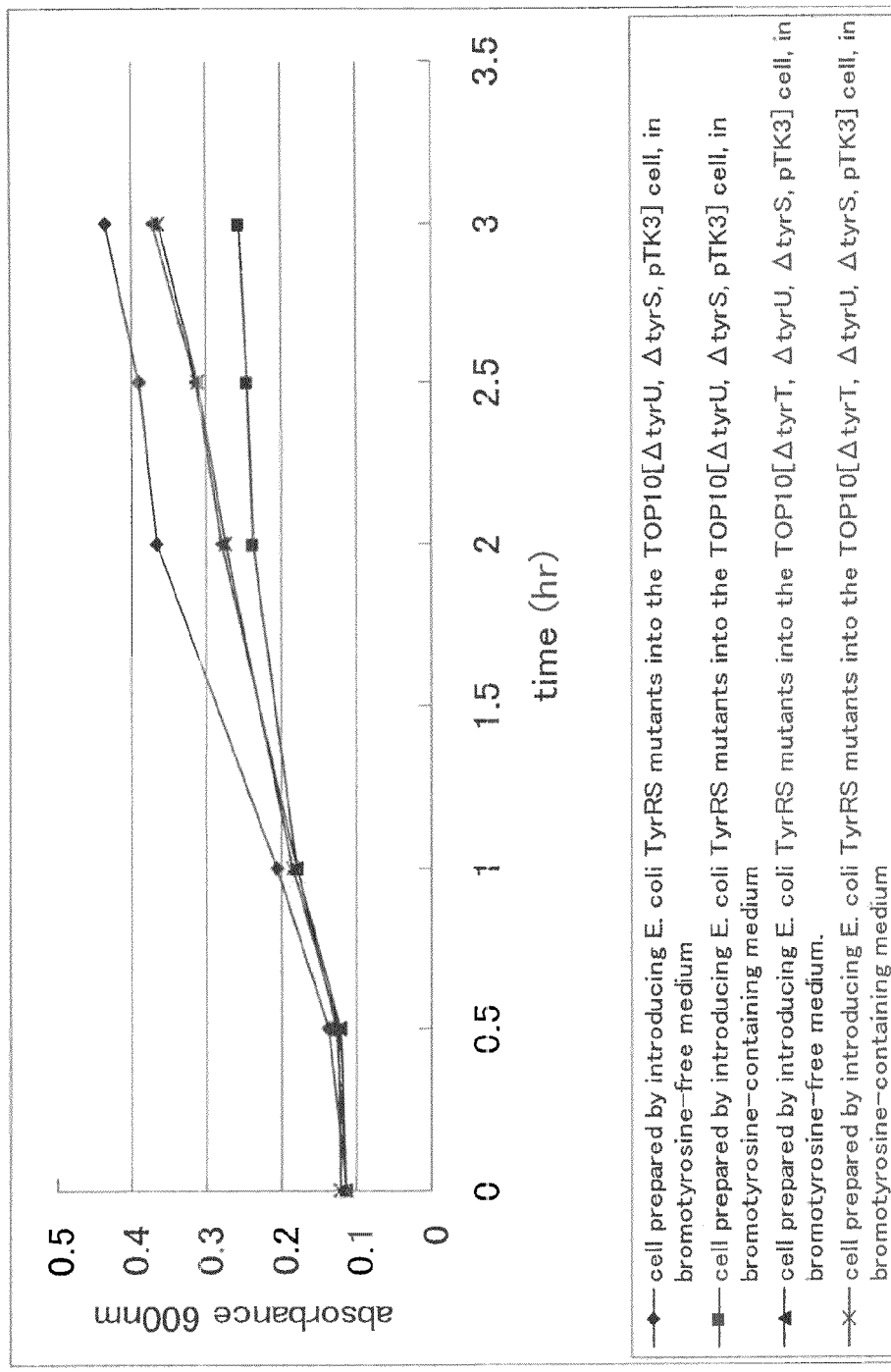
FIG. 2 shows growth curves attained by introducing E. coli TyrRS mutants into TOP10 [ΔtyrT, ΔtyrU, ΔtyrS, pTK3] and TOP10 [ΔtyrU, ΔtyrS, pTK3] cells and growing the same in bromotyrosine-containing medium and bromotyrosine-free medium.

FIG. 2 shows a growth curve attained by introducing *E. coli* TyrRS mutants into TOP10 [ΔtyrT, ΔtyrU, ΔtyrS, pTK3] and TOP10 [ΔtyrU, ΔtyrS, pTK3] cells and growing the same in bromotyrosine-containing medium and bromotyrosine-free medium.

In FIG. 2, cells prepared by introducing *E. coli* TyrRS mutants into the TOP10[ΔtyrU, ΔtyrS, pTK3] cells are indicated as "ΔtyrS," and cells prepared by introducing *E. coli* TyrRS mutants into the TOP10[ΔtyrT, ΔtyrU, ΔtyrS, pTK3] cells are indicated as "tyr-Mj." In FIG. 2, a horizontal axis shows a culture duration.

As is apparent from FIG. 2, a growth rate began to decrease upon addition of bromotyrosine, and growth stopped 2 hours later in the cells prepared by introducing E. con TyrRS mutants into the TOP10[ΔtyrU, ΔtyrS, pTK3] cells. This is because *E. coli* TyrRS mutants function due to the presence of the tyrT gene in the cells prepared by introducing *E. coli* TyrRS mutants into the TOP10[ΔtyrU, ΔtyrS, pTK3] cells. As is also apparent from FIG. 2, the addition of bromotyrosine did not influence the growth in cells prepared by introducing *E. coli* TyrRS mutants into the TOP10[ΔtyrT, ΔtyrU, ΔtyrS, pTK3] cells. This indicates that *E. coli* tyrosine tRNA has been completely knocked out and *E. coli* TyrRS mutants did not function in cells prepared by introducing *E. coli* TyrRS mutants into the TOP10[ΔtyrT, ΔtyrU, ΔtyrS, pTK3] cells.

Experimentation and Result-3

Subsequently, whether or not tyrT genes, tyrU genes, and tyrS genes had been completely removed from the genomes of the prepared TOP10[ΔtyrT, ΔtyrU, ΔtyrS, pTK3] cells was examined. Specifically, chromosome DNA was extracted from the TOP10[ΔtyrT, ΔtyrU, ΔtyrS, pTK3] cells, and PCR was carried out using the chromosome DNA as a template.

Chromosome DNA was extracted using the commercialized kit, Dr. GenTLE® (from Yeast) (Takara Bio Inc.). A pair of primers comprising the nucleotide sequences shown below was designed for each of the tyrT gene, the tyrU gene, and the tyrS gene, and the primers were chemically synthesized.

Nucleotide Sequences of Primers for tyrT Gene Amplification

```
                                      (SEQ ID NO: 20)
          GCAGGACGTTATTCATGTCG (SEQ ID NO: 21)
          GGGACTTTTGAAAGTGATGG
```

Nucleotide Sequences of Primers for tyrU Gene Amplification

```
                                      (SEQ ID NO: 22)
          GTAATCAGTAGGTCACCAGT (SEQ ID NO: 23)
          TTCGAGCCGGTAAGCGAACT
```

Nucleotide Sequences of Primers for tyrS Gene Amplification

```
                                      (SEQ ID NO: 24)
          AAAAGTCGTGTACCGGCAAAG (SEQ ID NO: 25)
          TAAACAACGTGAGACTGGATAG
```

Specifically, primers for tyrT gene amplification were designated as sequences in front of and behind the tyrT and tyrV genes. Primers for tyrU gene amplification were designated as sequences in front of and behind the tyrU gene. Primers for tyrS gene amplification were designated as sequences in front of and behind the tyrS gene.

Figure 3:
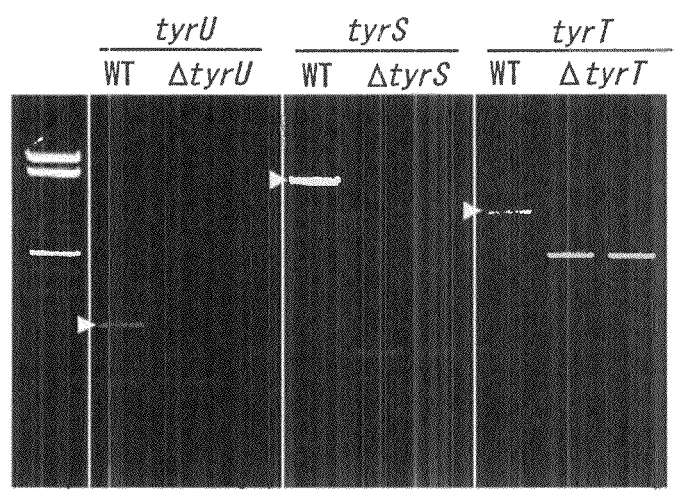
FIG. 3 is a photograph showing the results of extraction of chromosome DNAs from TOP10 [ΔtyrT, ΔtyrU, ΔtyrS, pTK3] and TOP10 cells, PCR and examination of PCR-amplified fragments via electrophoresis.

FIG. 3 shows the results of extraction of chromosome DNAs from TOP10 [ΔtyrT, ΔtyrU, ΔtyrS, pTK3] and wild-type TOP10 cells, PCR and examination of PCR-amplified fragments via electrophoresis. In FIG. 3, the results attained with the use of the TOP10 cells are indicated as "WT," and the results attained with the use of the TOP10[ΔtyrT, ΔtyrU., ΔtyrS, pTK3] cells are indicated as "ΔtyrU," "ΔtyrS," and "ΔtyrT." In FIG. 3, positions of amplified fragments that appear when amplifying the tyrT gene, the tyrU gene, and the tyrS gene with the use of chromosome DNA of the TOP 10 cell as a template are indicated by triangles.

As is apparent from FIG. 3, a fragment to be amplified became shorter when chromosome DNA of the TOP10 [ΔtyrT, ΔtyrU, ΔtyrS, pTK3] cells was used, compared with the fragment amplified with the use of chromosome DNA of the TOP10 cells. This demonstrates that the tyrT gene, the tyrU gene, and the tyrS gene had been completely removed from the genomes of the TOP10[ΔtyrT, ΔtyrU, ΔtyrS, pTK3] cells.

It was accordingly demonstrated that TyrRS and tyrosine tRNA inherent in the TOP10[ΔtyrT, ΔtyrU, ΔtyrS, pTK3] cells had been completely knocked out and that such TyrRS and tyrosine tRNA survived via translation of a tyrosine codons by archaebacteria TyrRS and tyrosine tRNA. Such TOP10[ΔtyrT, ΔtyrU, ΔtyrS, pTK3] cells can be used for production of alloproteins involving the use of E. coli-derived mutant TyrRS genes and suppressor tRNA$^{Tyr}$ genes.

Industrial Applicability

According to the method for producing proteins into which non-natural amino acids have been incorporated of the present invention, proteins into which non-natural amino acids have been incorporated at desired positions can be produced with the use of prokaryote-derived aminoacyl tRNA synthetase mutants and prokaryotic cells as host cells. The prokaryote-derived aminoacyl tRNA synthetase mutants can also be used for the method for producing proteins into which non-natural amino acids have been incorporated involving the use of eukaryote-type host cells. According to the present invention, therefore, prokaryote-derived aminoacyl tRNA synthetase mutants can be applied to either systems involving the use of prokaryotic or eukaryotic host cells.

According to the method for producing proteins into which non-natural amino acids have been incorporated, proteins into which non-natural amino acids have been incorporated at desired positions can be produced with the use of eukaryote-type aminoacyl tRNA synthetase mutants and eukaryotic host cells. The eukaryote-type aminoacyl tRNA synthetase mutants can also be applied to the method for producing proteins into which non-natural amino acids have been incorporated involving the use of prokaryotic host cells. According to the present invention, therefore, eukaryote-type aminoacyl tRNA synthetase mutants can be applied to either systems involving the use of prokaryotic or eukaryotic host cells.

All publications, patents, and patent applications cited herein are incorporated herein by reference in their entirety.

The invention claimed is:

1. A method for producing a protein into which a tyrosine analogue has been incorporated, wherein the method comprises:
(a) introducing a gene encoding a mutant tRNA synthetase (mtRS) derived from a yeast cell capable of binding to a tyrosine analogue, wherein said mtRS has a higher specificity for the tyrosine analogue compared to specificity for tyrosine; wherein the yeast host cell has a knockout of the endogenous tyrosyl-tRNA synthetase and tyrosine tRNA genes;
b) introducing a suppressor tRNA derived from the tyrosyl-tRNA gene of a yeast;
c) introducing an E. coli tyrosyl-tRNA synthetase and an E. coli tRNA genes specific for tyrosine into the yeast host cell; and
d) introducing a target gene having at least one suppressor codon at a specific site;
wherein the yeast host cell is cultured in a medium thereby expressing the target protein into which the tyrosine analogue is incorporated at the site encoded by the suppressor codon.

2. A yeast host cell, comprising
a mutant tRNA synthetase (mtRS) derived from a yeast cell capable of binding to a tyrosine analogue, wherein said mtRS has a higher specificity for the tyrosine analogue compared to specificity for tyrosine;
wherein the yeast host cell has a knockout of the endogenous tyrosyl-tRNA synthetase and tyrosine tRNA genes.

3. An extract of the yeast hot cell of claim 2.

4. A reagent kit configured for cell-free protein synthesis, the kit comprising:
a mutant tRNA synthetase (mtRS) derived from a yeast cell capable of binding to a tyrosine analogue, wherein said mtRS has a higher specificity for the tyrosine analogue compared to specificity for tyrosine;
an amino acid solution comprising the tyrosine analog; and the extract of claim 3.

5. A method for producing a target protein comprising a tyrosine analog, the method comprising
(1) introducing a target gene having at least one suppressor codon at a specific site into a yeast host cell, wherein the yeast host cell comprises (a) a gene encoding a mutant tRNA synthetase (mtRS) derived from a yeast cell capable of binding to a tyrosine analogue, wherein said mtRS has a higher specificity for the tyrosine analogue compared to specificity for tyrosine;
(b) a knockout of the endogenous tyrosyl-tRNA synthetase and tyrosine tRNA genes;
(c) a suppressor tRNA derived from the tyrosyl-tRNA gene of a yeast; and
(d) an *E. coli* tyrosyl-tRNA synthetase and an *E. coli* tRNA genes specific for tyrosine;
(2) culturing the yeast host cell in a medium thereby expressing the target protein into which a tyrosine analogue is incorporated at the site encoded by the suppressor codon; and
(3) recovering the target protein comprising a tyrosine analog.

6. The method according to claim 1, wherein the tyrosine analog is a 3-substituted tyrosine or a 4-substituted tyrosine.

7. The method according to claim 1, wherein the tyrosine analog is a 3-substituted tyrosine and which is a 3-halogenated tyrosine.

8. The method according to claim 1, wherein the tyrosine analog is a 4-substituted tyrosine which is 4-acetyl-L-phenylalanine, 4-benzoyl-L-phenylalanine, 4-azide-L-phenylalanine, O-methyl-tyrosine, or 4-iodo-L-phenylalanine.

9. The method according to claim 5, wherein the tyrosine analog is a 3-substituted tyrosine or a 4-substituted tyrosine.

10. The method according to claim 5, wherein the tyrosine analog is a 3-substituted tyrosine and which is a 3-halogenated tyrosine.

11. The method according to claim 5, wherein the tyrosine analogy is a 4-substituted tyrosine which is 4-acetyl-L-phenylalanine, 4-benzoyl-L-phenylalanine, 4-azide-L-phenylalanine, O-methyl-tyrosine, or 4-iodo-L-phenylalanine.

* * * * *